: US 12,180,148 B2
(45) Date of Patent: *Dec. 31, 2024

(12) United States Patent
Xu et al.

(54) CATALYTIC CONVERSION PROCESS AND SYSTEM WITH INCREASED PROPYLENE PRODUCTION

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Youhao Xu, Beijing (CN); Xuhui Bai, Beijing (CN); Langyou Wen, Beijing (CN); Xin Wang, Beijing (CN); Mingyuan He, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

(*) Notice: Subject to any disclaimer, the term of this patent is extended or adjusted under 35 U.S.C. 154(b) by 428 days.

This patent is subject to a terminal disclaimer.

(21) Appl. No.: 17/442,039

(22) PCT Filed: Mar. 17, 2020

(86) PCT No.: PCT/CN2020/079655
§ 371 (c)(1),
(2) Date: Sep. 22, 2021

(87) PCT Pub. No.: WO2020/192490
PCT Pub. Date: Oct. 1, 2020

(65) Prior Publication Data
US 2022/0177390 A1 Jun. 9, 2022

(30) Foreign Application Priority Data

Mar. 22, 2019 (CN) .......................... 201910224119.X

(51) Int. Cl.
C07C 4/06 (2006.01)
B01J 8/24 (2006.01)
(Continued)

(52) U.S. Cl.
CPC .................................... C07C 4/06 (2013.01);
B01J 8/24 (2013.01); B01J 27/16 (2013.01);
B01J 29/76 (2013.01);
(Continued)

(58) Field of Classification Search
None
See application file for complete search history.

(56) References Cited

U.S. PATENT DOCUMENTS 3,702,886 A   11/1972 Argauer et al.
3,771,966 A * 11/1973 Hutson, Jr. ............... C07C 2/28
                                              585/924
(Continued)

FOREIGN PATENT DOCUMENTS

CN   1237477 A   12/1999
CN   1642887 A    7/2005
(Continued)

Primary Examiner — In Suk C Bullock
Assistant Examiner — Alyssa L Cepluch
(74) Attorney, Agent, or Firm — NKL Law; Allen Xue

(57) ABSTRACT

A catalytic conversion process for producing propylene includes the steps of: 1) providing a starting material comprising olefin(s) having 4 or more carbon atoms; 2) pretreating the starting material to obtain a propylene precursor comprising olefin(s) having $3\times2^n$ carbon atoms, wherein n is an integer greater than or equal to 1; and 3) subjecting the propylene precursor to a catalytic cracking reaction to obtain a reaction product comprising propylene.

12 Claims, 4 Drawing Sheets

(51) Int. Cl.
  *B01J 27/16* (2006.01)
  *B01J 29/76* (2006.01)
  *B01J 35/61* (2024.01)
  *B01J 35/63* (2024.01)
  *C07C 2/18* (2006.01)

(52) U.S. Cl.
  CPC ........... *B01J 35/615* (2024.01); *B01J 35/635* (2024.01); *C07C 2/18* (2013.01); *C07C 2529/072* (2013.01)

(56) References Cited

U.S. PATENT DOCUMENTS

| | | | |
|---|---|---|---|
| 5,232,675 A | 8/1993 | Shu et al. | |
| 6,049,017 A | 4/2000 | Vora et al. | |
| 6,342,153 B1* | 1/2002 | Guan | B01J 20/10 502/79 |
| 7,678,342 B1* | 3/2010 | Xu | C10G 11/18 422/142 |
| 9,834,492 B2 | 12/2017 | Nicholas et al. | |
| 11,873,457 B2* | 1/2024 | Bai | C10G 69/126 |
| 11,905,227 B2* | 2/2024 | Li | C07C 2/12 |
| 2005/0121361 A1* | 6/2005 | Duplan | C10G 69/126 208/78 |
| 2005/0222475 A1* | 10/2005 | Duplan | C07C 2/12 585/329 |
| 2009/0264693 A1* | 10/2009 | Xie | C10G 11/16 585/653 |
| 2011/0000818 A1 | 1/2011 | Xu et al. | |
| 2013/0178672 A1* | 7/2013 | Chen | C10G 11/182 585/324 |
| 2014/0135539 A1 | 5/2014 | Nicholas et al. | |
| 2015/0376090 A1 | 12/2015 | Mehlberg et al. | |
| 2015/0376515 A1 | 12/2015 | Lim et al. | |

FOREIGN PATENT DOCUMENTS

| | | |
|---|---|---|
| CN | 1670133 A | 9/2005 |
| CN | 1915923 A | 2/2007 |
| CN | 1923971 A | 3/2007 |
| CN | 101134913 A | 3/2008 |
| CN | 101381272 A | 3/2009 |
| CN | 103131463 A | 6/2013 |
| CN | 103333714 A | 10/2013 |
| CN | 103814002 A | 5/2014 |
| CN | 109369319 A | 2/2019 |
| WO | 0104237 A2 | 1/2001 |
| WO | 2010023369 A1 | 3/2010 |
| WO | WO-2012076758 A2 * | 6/2012 ............. C10G 11/18 |

* cited by examiner

CATALYTIC CONVERSION PROCESS AND SYSTEM WITH INCREASED PROPYLENE PRODUCTION

CROSS REFERENCE TO RELATED APPLICATIONS

The present application is a U.S. national stage entry of International Application No. PCT/CN2020/079655, filed Mar. 17, 2020, which claims the priority of Chinese patent application No. 201910224119.X, titled "catalytic conversion process and system with increased propylene production", filed on Mar. 22, 2019, which is incorporated herein by reference in its entirety.

TECHNICAL FIELD

The present application relates to the field of catalytic conversion of hydrocarbons, particularly to a catalytic conversion process and system with increased propylene production.

BACKGROUND ART

Propylene is an important petrochemical raw material, and with the continuous development of new varieties of propylene derivatives, the demand for propylene is vigorous in recent years. At present, in China, 54% of propylene is produced by steam cracking of naphtha, of which the propylene yield is only about 15 wt %, 42% of propylene is produced as a byproduct of catalytic cracking units, and a small amount (about 2%) of propylene is produced by propane dehydrogenation and ethylene-butene metathesis reaction.

If ethylene and propylene are produced along the traditional route of steam cracking in the petrochemical industry, there may be a plurality of restriction factors, such as shortage of light feedstock oil, insufficient production capacity, excessive cost, etc. Catalytic Cracking (FCC) is gaining more and more attention due to its advantages of wide raw material adaptability, flexible operation, etc. The development of a new propylene production technology has important practical significance for further widening the source of propylene.

International patent application publication No. WO2001004237A2 describes a process for the production of propylene from light olefins in one step, which can be considered as a variation of the FCC process utilizing a catalyst containing a ZSM-5 zeolite. Typical operating conditions for this process include a temperature close to 600° C. and a pressure of 0.1-0.2 MPa. Propylene yield is about 30% under such conditions, which can be increased to 50% by the recycle of unreacted $C_4$ and $C_5$ fractions. The disadvantage of this process is that the fluidized bed technique is expensive from an investment point of view and requires relatively sensitive control of the process. In addition, the catalyst is lost considerably as a result of its consumption.

U.S. Pat. No. 6,049,017 describes a process for the production of ethylene and propylene from an olefin fraction, comprising the steps of: a) separating ethylene, propylene, and then diene (e.g., by selective hydrogenation); b) separating normal olefins and isoolefins by conversion of isoolefins using an oxygenate (e.g., methanol, ethanol, etc.) and an acid catalyst to form oxygenates; c) separating the oxygenated compounds; d) cracking the normal olefins using microporous catalysts (e.g., zeolite catalysts or non-zeolite catalysts preferably containing SAPOs) to produce ethylene and propylene. According to the description of this patent: since isoolefins (such as isobutylene, etc.) cannot be easily converted into products such as ethylene and propylene during the cracking process described, isoolefins are separated from normal olefins by a process of converting isoolefins into oxygenates; normal olefins are fed to a cracking reactor together with paraffins, and normal olefins undergo a cracking reaction therein to produce target products such as propylene and ethylene. This patent also describes that: since paraffins are not reacted in the cracking reactor, in order to prevent the paraffins from accumulating in the cracking reactor, it is necessary to extract part of the reaction material for use in preparing other fuels or to convert the olefins into heavier components by oligomerization and then separate them from the paraffins, and the olefin stream obtained after oligomerization is partially or completely returned to the cracking reactor. From the above description it can be seen that: in the process described in this patent, the material entering the reactor is mainly a mixture of unconverted and unseparated normal olefins and alkanes, and the olefins are reacted in the reactor to produce the target product. Alkanes are present as an inert component in the reaction system. The separation of olefins from n-paraffins having a similar boiling point is not carried out, or the separation is carried out by oligomerizing the olefins.

Chinese patent application publication No. CN103333714A describes another process: after $C_4/C_5$ olefin fraction from steam cracking or catalytic cracking process is respectively subjected to selective hydrogenation to remove diene and selective oligomerization to remove isobutene, n-butene and unseparated alkane components are sent together to a cracking reactor, where the n-butene is cracked to generate target products such as ethylene, propylene and the like, and the alkane remains unchanged. The $C_4$ component obtained at the outlet of the reactor is recycled to the inlet of the cracking reactor for further reaction. It can be seen that the process also suffers from the accumulation of an inert component, i.e. alkanes, in the cracking reactor. To avoid this problem, a part of the reaction stream has to be withdrawn from the cracking reactor, and thus a part of the $C_4$ olefins that can be cracked will also be withdrawn at the same time, affecting the efficiency of the utilization of the feedstock. In order to ensure the utilization efficiency of the reactive $C_4$ olefins in the feedstock, it is necessary to introduce a method for separating the alkanes and olefins.

Chinese patent application publication No. CN101381272A discloses a process for preparing ethylene and propylene from methanol and $C_4$ olefin in two steps. In the process, methanol, dimethyl ether and olefin having 4 or more carbon atoms are firstly subjected to an etherification reaction, and then the reaction effluent is subjected to a cracking reaction to produce ethylene and propylene. However, the process is mainly designed for achieving a full heat utilization and a reduction of reaction temperature by combining the production of olefin from methanol and the production of olefin by cracking of $C_4$ olefins. The process does not involve the separation of alkane and olefin, and if a catalytic cracking device is adopted for cracking reaction, the problems of heavy load and high energy consumption of the device caused by accumulation of alkane in the system are still difficult to be solved. In addition, the process described in this patent application, in which olefins having four or more carbon atoms are etherified with dimethyl ether (methyl alkyl ether and methanol are produced), and the product is recycled, still takes the step of producing olefins by methanol cracking as a necessary step of the whole reaction process.

As can be seen from the above overview: in existing processes for producing propylene in high yield from light olefins through catalytic cracking or cracking, the main staring material is liquefied gas from steam cracking or catalytic cracking apparatus, which is passed to an etherifying apparatus after removal of $C_2$, $C_3$ and $C_5$ in gas separating apparatus, and then the etherified $C_4$ component free of isobutene or light gasoline rich in olefins is cracked directly without alkane/olefin separation. As alkanes are continuously accumulated in the system, the olefin content recycled in the system is low. Therefore, a part of the $C_4$ component with a low olefin content has be discharged from the system in the process, and the process has the disadvantages of low propylene selectivity of the cracking, heavy load and high energy consumption.

Chinese patent application publication No. CN103814002A discloses a process for the oligomerization of hydrocarbon(s), which comprises oligomerizing a feed comprising one or more $C_3$-$C_5$ hydrocarbons to produce an effluent, and recycling at least a part of the oligomerized effluent to produce propylene in a high yield. In the process, one or more $C_8^+$ hydrocarbons, such as $C_8$, $C_9$, $C_{12}$, $C_{16}$ and $C_{20}$ olefins, are produced in the oligomerization reaction zone.

There remains a need in the art for a catalytic conversion process and system that can produce propylene in a high yield while eliminating or overcoming at least some of the deficiencies of the prior arts described above.

SUMMARY OF THE INVENTION

It is an object of the present application to provide a catalytic conversion process and system for producing propylene in high yield, which can provide a high propylene yield and selectivity, as well as a low alkane yield, especially low methane and ethane yields.

In order to achieve the above object, in an aspect, the present application provides a process for producing propylene, comprising the steps of:
1) providing a starting material comprising olefin(s) having 4 or more carbon atoms;
2) pretreating the starting material to obtain a propylene precursor comprising olefin(s) having $3\times2^n$ carbon atoms, wherein n is an integer greater than or equal to 1, preferably 1-3, more preferably 1-2; and
3) subjecting the propylene precursor to a catalytic cracking reaction to obtain a reaction product comprising propylene, wherein the pretreating of step 2) comprises one or both of:
2a) separating the starting material to obtain a first propylene precursor comprising olefin(s) having $3\times2^n$ carbon atoms, and/or one or more of the following fractions: a fraction comprising $C_4$ olefin, a fraction comprising $C_5$ olefin, a fraction comprising $C_7$ olefin, and a fraction comprising $C_8$ olefin; and
2b) subjecting the starting material or a fraction thereof to an olefin oligomerization reaction, and optionally separating the resulting oligomerization product, to obtain a second propylene precursor comprising olefin(s) having $3\times2^m$ carbon atoms, wherein m is an integer greater than or equal to 2, preferably 2 to 3.

Preferably, said step 1) further comprises subjecting a hydrocarbon feedstock to a catalytic conversion reaction to obtain a reaction product comprising olefin(s) having 4 or more carbon atoms as the starting material.

In another aspect, the present application provides a system for producing propylene, comprising a pretreatment unit configured to pretreat a starting material comprising olefin(s) having 4 or more carbon atoms to obtain a propylene precursor comprising olefin(s) having $3\times2^n$ carbon atoms, wherein n is an integer greater than or equal to 1, preferably 1 to 3, more preferably 1 to 2, and a reaction unit configured to catalytically crack the propylene precursor to obtain a reaction product comprising propylene, wherein the pretreatment unit comprises at least one of a first separation unit configured to separate the starting material to obtain a first propylene precursor comprising olefin(s) having $3\times2^n$ carbon atoms, and/or one or more of the following fractions: a fraction comprising $C_4$ olefin, a fraction comprising $C_5$ olefin, a fraction comprising $C_7$ olefin, and a fraction comprising $C_8$ olefin; and an oligomerization unit configured to carry out an olefin oligomerization reaction on the starting material or a fraction thereof, and optionally separate the resulting oligomerization product, to obtain a second propylene precursor comprising olefin(s) having $3\times2^m$ carbon atoms, wherein m is an integer greater than or equal to 2, preferably 2 to 3.

Preferably, the reaction unit comprises a catalytic conversion reaction device, an oil-catalyst separation device and a regenerator, wherein the catalytic conversion reaction device is configured to perform a catalytic conversion reaction on a hydrocarbon feedstock in the presence of a catalyst to obtain a reaction effluent comprising a catalytic conversion product and a spent catalyst, wherein the catalytic conversion product comprises olefin(s) having 4 or more carbon atoms and optionally propylene, the oil-catalyst separation device is configured to separate the catalytic conversion product from the spent catalyst in the reaction effluent, and transport the catalytic conversion product to the pretreatment unit to serve as the starting material;

the regenerator is configured to regenerate the spent catalyst and recycle the regenerated catalyst to the catalytic conversion reaction device; and the pretreatment unit is configured to pretreat the starting material to obtain the propylene precursor comprising olefin(s) having $3\times2^n$ carbon atoms and optionally a propylene product, and recycle the propylene precursor to the catalytic conversion reaction device.

Compared with the prior arts, the process and system of the present application have one or more of the following advantages:
(1) capable of separating olefins having $3\times2^n$ carbon atoms that are easy to be cracked to generate propylene from the reaction product obtained by catalytic conversion, and further cracking them to generate propylene, thereby improving the propylene yield;
(2) capable of separating specific olefins (such as $C_4$, $C_5$, $C_7$ and $C_8$ olefins) from the reaction product obtained by catalytic conversion, carrying out targeted oligomerization on the specific olefins to obtain olefins having $3\times2^n$ carbon atoms, and further cracking them to generate propylene, thereby improving the propylene yield to the maximum extent; and
(3) combining the olefin oligomerization process with the catalytic conversion process, so that the reaction conditions can be flexibly controlled, the target reaction can be effectively promoted, and the target product can be increased.

Additional characteristics and advantages of the present application will be described in detail hereinbelow.

BRIEF DESCRIPTION OF THE DRAWINGS

The drawings, forming a part of the present description, are provided to help the understanding of the present application, and should not be considered to be limiting. The present application can be interpreted with reference to the drawings in combination with the detailed description hereinbelow. In the drawings.

Figure 1:
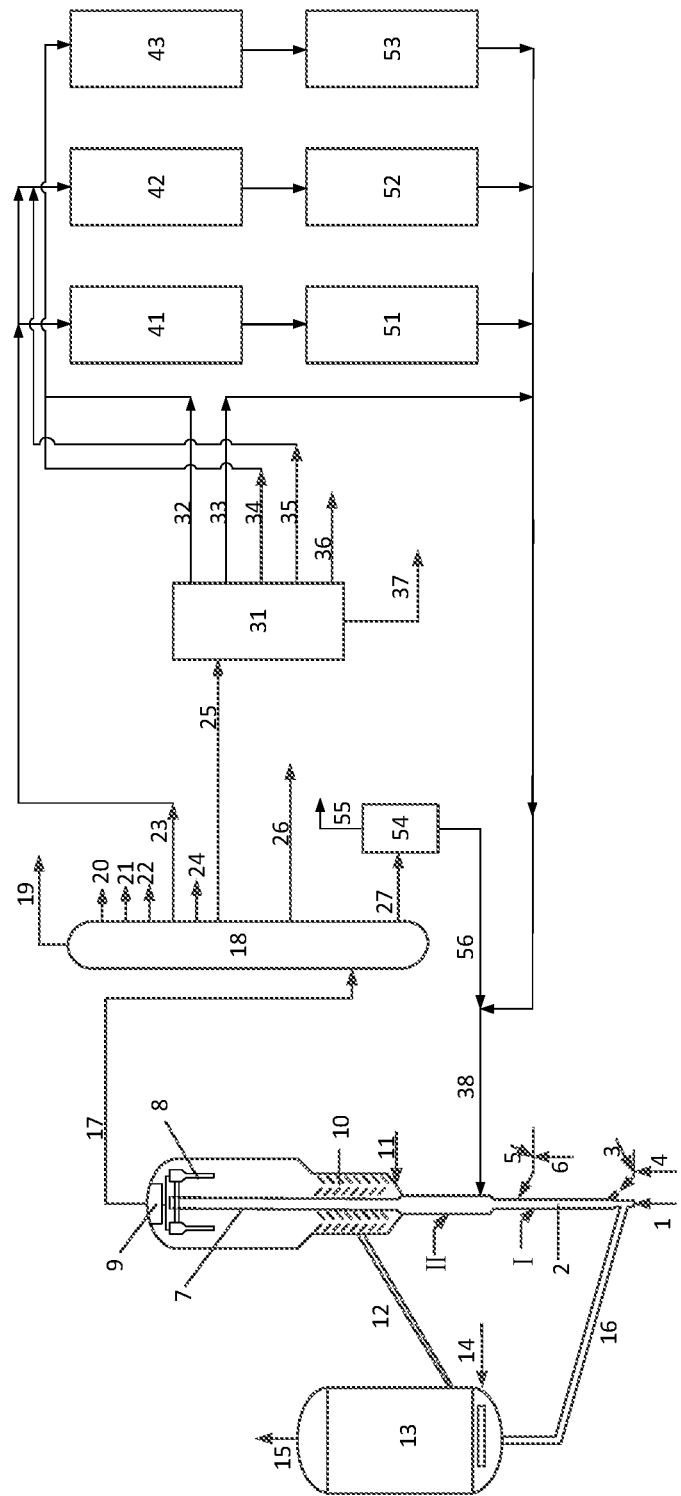
FIG. 1 is a schematic diagram of a first embodiment of the process and system of the present application.

| Description of the reference numerals | | |
|---|---|---|
| I first reaction zone | II second reaction zone | |
| 1 pipeline | 2 diameter-transformed riser reactor | 3 pipeline |
| 4 pipeline | 5 pipeline | 6 pipeline |
| 7 outlet section | 8 disengager | 9 gas collection chamber |
| 10 stripping section | 11 pipeline | 12 standpipe |
| 13 regenerator | 14 pipeline | 15 pipeline |
| 16 pipeline | 17 vapor line | 18 product separation unit |
| 19 pipeline | 20 pipeline | 21 pipeline |
| 22 pipeline | 23 pipeline | 24 pipeline |
| 25 pipeline | 26 pipeline | |
| 31 olefin separation device | 32 pipeline | 33 pipeline |
| 34 pipeline | 35 pipeline | 36 pipeline |
| 37 pipeline | 38 pipeline | |
| 41 oligomerization reactor | 42 oligomerization reactor | 43 oligomerization reactor |
| 51 rectifying column | 52 rectifying column | 53 rectifying column |
| 54 hydrotreating reactor | 55 pipeline | 56 pipeline |
| 2A riser unit | 2B dense phase bed unit | |
| 201 pipeline | 203 pipeline | 204 pipeline |
| 205 pipeline | 206 pipeline | 207 pipeline |
| 208 disengager | 209 gas collection chamber | 210 stripping section |
| 211 pipeline | 212 standpipe | 213 regenerator |
| 214 pipeline | 215 pipeline | 216 pipeline |
| 217 vapor line | | |
| 3A first reaction zone | 3B second reaction zone | |
| 301 pipeline | 302 diameter-transformed riser reactor | 303 pipeline |
| 304 pipeline | 305 pipeline | 306 pipeline |
| 307 pipeline | 308 disengager | 309 gas collection chamber |
| 310 stripping section | 311 pipeline | 312 standpipe |
| 313 regenerator | 314 pipeline | 315 pipeline |
| 316 pipeline | 317 vapor line | |
| 4A first riser reactor | 4B second riser reactor | |
| 401 pipeline | 403 pipeline | 404 pipeline |
| 405 pipeline | 406 stripping section | 407 outlet section |
| 408 disengager | 409 gas collection chamber | 410 vapor line |
| 411 standpipe | 412 regenerator | 413 pipeline |
| 414 pipeline | 415 pipeline | 416 pipeline |
| 417 standpipe | 421 pipeline | 423 pipeline |
| 425 pipeline | 426 stripping section | 427 outlet section |
| 428 disengager | 429 gas collection chamber | 430 vapor line |
| 431 pipeline | | |

DETAILED DESCRIPTION OF THE INVENTION

The present application will be further described hereinafter in detail with reference to particular embodiments thereof and the accompanying drawings. It should be noted that the particular embodiments of the present application are provided for illustration purpose only, and are not intended to be limiting in any manner.

As described above, in a first aspect, the present application provides a process for producing propylene, comprising the steps of:

1) providing a starting material comprising olefin(s) having 4 or more carbon atoms;

2) pretreating the starting material to obtain a propylene precursor comprising olefin(s) having $3 \times 2^n$ carbon atoms, wherein n is an integer greater than or equal to 1, preferably 1-3, more preferably 1-2; and 3) subjecting the propylene precursor to a catalytic cracking reaction to obtain a reaction product comprising propylene, wherein the pretreating of step 2) comprises one or both of:

2a) separating the starting material to obtain a first propylene precursor comprising olefin(s) having $3 \times 2^n$ carbon atoms, and/or one or more of the following fractions: a fraction comprising $C_4$ olefin, a fraction comprising $C_5$ olefin, a fraction comprising $C_7$ olefin, and a fraction comprising $C_8$ olefin; and 2b) subjecting the starting material or a fraction thereof to an olefin oligomerization reaction, and optionally separating the resulting oligomerization product, to obtain a second propylene precursor comprising olefin(s) having $3 \times 2^m$ carbon atoms, wherein m is an integer greater than or equal to 2, preferably 2 to 3.

In a preferred embodiment, in the separation step 2a), based on the weight of the resulting first propylene precursor, the first propylene precursor has a $C_6$ olefin content of no less than about 40 wt %, more preferably no less than about 70 wt %, even more preferably no less than about 80 wt %, especially preferably no less than about 90 wt %, and is most preferably consisted essentially of $C_6$ olefin.

In a preferred embodiment, said oligomerization step 2b) comprises one or more of the following:

b1) subjecting the fraction comprising $C_4$ olefin (also referred to as $C_4$ olefin-containing fraction) of the starting material to an olefin oligomerization reaction, and optionally separating the resulting oligomerization product, to obtain the second propylene precursor that comprises $C_{12}$ olefin;

b2) combining the $C_5$ olefin-containing fraction with the $C_7$ olefin-containing fraction of the starting material to obtain an oligomerization feedstock, subjecting the oligomerization feedstock to an oligomerization reaction, and optionally separating the resulting oligomerization product, to obtain the second propylene precursor that comprises $C_{12}$ olefin; and b3) combining the $C_4$ olefin-containing fraction with the $C_8$ olefin-containing fraction of the starting material to provide an oligomerization feedstock, subjecting the oligomerization feedstock to an oligomerization reaction, and optionally separating the resulting oligomerization product to provide the second propylene precursor that comprises $C_{12}$ olefin.

The inventors of the present application have unexpectedly found during the course of experiments that olefins having $3 \times 2^n$ carbon atoms, where n is an integer greater than or equal to 1, especially $C_6$ and $C_{12}$ olefins, have a high selectivity to propylene when being cracked. Thus, the process of the present application intentionally separates olefin(s) having $3 \times 2^n$ carbon atoms from the reaction feedstock (such as catalytic conversion product), and/or separates specific olefins (such as $C_4$, $C_5$, $C_7$ and $C_8$ olefins) from the reaction feedstock, selectively coverts them into olefins having $3 \times 2^n$ carbon atoms by oligomerization, and then carries out catalytic cracking on the olefins having $3 \times 2^n$ carbon atoms, thereby obtaining a higher propylene yield and realizing an effective utilization of petroleum resources.

The oligomerization reaction is well known to those skilled in the art, and is used in the present application for converting various olefins to olefin(s) having $3 \times 2^n$ carbon atoms, such as $C_{12}$ olefin, by oligomerization. In a preferred embodiment, each of the oligomerization reactions involved in the process of the present application, for example the oligomerization reactions involved in steps 2b), b1), b2), and b3), is carried out independently in the presence of an oligomerization catalyst under conditions including: a temperature of about 50-550° C., preferably about 400-550° C., a pressure of about 0.2-8.0 MPa, preferably about 0.5-4 MPa, and a weight hourly space velocity of about 0.1-10 preferably about 1-6 $h^{-1}$.

In a further preferred embodiment, in the oligomerization step b2), the weight ratio of $C_5$ olefin to $C_7$ olefin in the oligomerization feedstock is about 1:0.7 to about 1:3; and/or, in the oligomerization step b3), the weight ratio of $C_4$ olefin to $C_8$ olefin in the oligomerization feedstock is about 1:0.5 to about 1:3.

According to the present application, the oligomerization catalysts may each be independently one or more selected from the group consisting of phosphoric acid catalysts, acidic resins, silica-alumina solid acid catalysts, and zeolite solid acid catalysts. The phosphoric acid catalyst can be one or more of a catalyst formed by loading phosphoric acid on diatomite, a catalyst formed by loading phosphoric acid on activated carbon, a catalyst formed by phosphoric acid-soaked quartz sand, a catalyst formed by loading phosphoric acid on silica gel and a catalyst formed by loading copper pyrophosphate on silica gel; the silica-alumina solid acid catalyst can be a catalyst formed by loading metal ion(s) on alumina and/or amorphous silica-alumina carrier, wherein the loaded metal ion(s) can be selected from Group VIII metals, Group IVA metals or a combination thereof; the zeolite solid acid catalyst may comprise about 10-100 wt % of a zeolite and about 0-90 wt % of a matrix, based on the weight of the zeolite solid acid catalyst, wherein the zeolite is one or more selected from the group consisting of one-dimensional zeolites, two-dimensional zeolites, and three-dimensional zeolites, preferably the one-dimensional zeolite is selected from the group consisting of MTW (ZSM-12), MTT (ZSM-23), and TON (ZSM-22), the two-dimensional zeolite is selected from the group consisting of FER (ferrierite), MFS (ZSM-57), MWW (MCM-22), and MOR (mordenite), and the three-dimensional zeolite is selected from the group consisting of beta zeolites. Further preferably, the zeolite is selected from ZSM-5 zeolites. In the present application, the one-, two- and three-dimensional zeolites are classified according to the characteristics of the channel system of the zeolite, and of which the meaning is well known to those skilled in the art and the detailed description is omitted herein for brevity.

The oligomerization reaction involved in the present application is one in which reaction conditions are controlled and catalyst is carefully selected to maximize the production of $C_{12}$ olefin, for example, in the oligomerization steps 2b), b1), b2), and b3), the $C_{12}$ olefin contents of the resulting oligomerization products may each be no less than about 40 wt %, preferably no less than about 50 wt %, more preferably no less than about 70 wt %, and most preferably no less than about 80 wt %, based on the weight of the oligomerization product. Preferably, the resulting second propylene precursors each independently has a $C_{12}$ olefin content of no less than about 40 wt %, preferably no less than about 50 wt %, more preferably no less than about 70 wt %, even more preferably no less than about 80 wt %, especially preferably no less than about 90 wt %, based on the weight of the second propylene precursor, and is most preferably consisted essentially of $C_{12}$ olefin.

In addition, according to the present application, the oligomerization reaction can be further promoted by optimizing the olefin content and the impurities content of the olefin-containing fractions. For example, the $C_4$ olefin-containing fraction preferably has a $C_4$ olefin content of about 40-100 wt %, based on the weight of the $C_4$ olefin-containing fraction; the $C_5$ olefin-containing fraction preferably has a $C_5$ olefin content of about 40-100 wt %, based on the weight of the $C_5$ olefin-containing fraction; the $C_7$ olefin-containing fraction preferably has a $C_7$ olefin content of about 40-100 wt %, based on the weight of the $C_7$ olefin-containing fraction; and/or the $C_8$ olefin-containing fraction preferably has a $C_8$ olefin content of about 40-100 wt %, based on the weight of the $C_8$ olefin-containing fraction.

According to the present application, it is preferable that the oligomerization feedstock (e.g., each fraction comprising the specified olefin) be pretreated prior to the oligomerization reaction, so that it may have a sulfur content of no more than about 20 µg/g, a basic nitride content of no more than about 0.6 µg/g, a water content of about 600-1800 µg/g, and a diene content of no more than about 200 µg/g.

According to the present application, in order to further improve the utilization rate of olefins, the process may further comprise: recycling the oligomerization product residue obtained after separating out the second propylene precursor comprising $C_{12}$ olefin to the oligomerization reactor for further oligomerization reaction, or further separating the oligomerization product residue obtained after separating out the second propylene precursor comprising $C_{12}$ olefin into $C_4$ olefin, $C_5$ olefin, $C_7$ olefin and $C_8$ olefin, and then recycling the $C_4$ olefin, $C_5$ olefin, $C_7$ olefin and $C_8$ olefin for further oligomerization reaction.

In a preferred embodiment, said step 1) further comprises subjecting a hydrocarbon feedstock to a catalytic conversion reaction to obtain a reaction product comprising olefin(s) having 4 or more carbon atoms as the starting material. The feedstock for the catalytic conversion reaction involved in the present application may be well known to those skilled in the art, for example, the feedstock may be selected from petroleum hydrocarbons, which may be one or more selected from the group consisting of vacuum gas oil (VGO), atmospheric gas oil (AGO), coker gas oil (CGO), deasphalted oil (DAO), vacuum residue (VR), atmospheric residue, and heavy aromatic raffinate oil, other mineral oils, which may be one or more selected from the group consisting of coal liquefaction oil, oil sand's oil, and shale oil, or combinations thereof. The petroleum hydrocarbon can be a full or partial fraction that is not hydrogenated, or a full or partial fraction that has been hydrogenated.

According to the present application, the reaction devices used for the catalytic conversion reaction of step 1) and the catalytic cracking reaction of step 3) may be well known to those skilled in the art, and for example, the reaction devices used in the respective steps may be each independently selected from fluidized bed reactors.

In the present application, the term "fluidized bed reactor" should be understood in its broadest sense, which includes various forms of reactors for bringing a gaseous feedstock into contact with solid catalyst particles in a fluidized state for a chemical reaction therein, including, but not limited to, dense phase bed, bubbling bed, turbulent bed, fast bed, gas phase transport bed (e.g., upward bed, downer bed), and the like, and may be a constant-linear-velocity fluidized bed reactor, an equal-diameter fluidized bed reactor, a diameter-transformed fluidized bed reactor, and the like, or alternatively a composite reactor resulting from a combination of two or more different types of fluidized beds connected in series, and is preferably a riser reactor or a composite reactor combining a riser with a dense phase bed. Typically, the gas velocity of the dense phase bed is in a range of about 0.1-2 m/s, while the gas velocity of the riser is in a range of about 2-30 m/s (excluding the catalyst). In a preferred embodiment, the riser reactor may be an equal-diameter riser reactor or a diameter-transformed riser reactor.

According to the present application, the catalytic conversion reaction of step 1) and the catalytic cracking reaction of step 3) may be carried out in separate reaction devices, or may be carried out in the same or different parts of the same reaction device. In a preferred embodiment, the catalytic conversion reaction of step 1) and the catalytic cracking reaction of step 3) are carried out in the same reaction device, which may be selected from a composite reactor consisting of a riser and a dense phase bed connected in series or a diameter-transformed riser reactor. For example, the two can be carried out in a diameter-transformed riser reactor as disclosed in Chinese patent application publication No. CN1237477A, which is incorporated herein by reference in its entirety.

According to the present application, the catalytic conversion reaction of step 1) and the catalytic cracking reaction of step 3) can be carried out in the presence of the same or different catalysts, preferably in the presence of the same catalyst in the same reactor.

Catalysts for the catalytic conversion reaction of step 1) and the catalytic cracking reaction of step 3) of the present application may be well known to those skilled in the art. For example, the catalysts used for the catalytic conversion reaction of step 1) and the catalytic cracking reaction of step 3) may each independently comprise about 1-50 wt % of zeolite, about 5-99 wt % of inorganic oxide, and about 0-70 wt % of clay, based on the weight of the catalyst. In the catalyst, the zeolite is used as an active component, and the zeolite may be selected from mesoporous zeolite, macroporous zeolite, or a combination thereof. Preferably, the mesoporous zeolite may account for about 50-100 wt %, preferably about 70-100 wt %, and the macroporous zeolite may account for about 0-50 wt %, preferably about 0-30 wt %, of the total weight of the zeolite. The mesoporous zeolite may be selected from ZSM series zeolites, ZRP zeolites, or combinations thereof. Optionally, the mesoporous zeolite may be modified with a nonmetallic element such as phosphorus and/or a transition metal element such as iron, cobalt, or nickel. For a more detailed description of ZRP zeolites, reference may be made to U.S. Pat. No. 5,232,675, which is incorporated herein by reference in its entirety. The ZSM-series zeolites may be selected from the group consisting of ZSM-5, ZSM-11, ZSM-12, ZSM-22, ZSM-35, ZSM-38, ZSM-48, other zeolites having similar structure, or mixtures thereof. More detailed description of ZSM-5 and the like may be found in U.S. Pat. No. 3,702,886, which is incorporated herein by reference in its entirety. The macroporous zeolite may be one or more selected from the group consisting of REY zeolite, REHY zeolite, ultrastable Y zeolite and high-silica Y zeolite. In the catalyst, the inorganic oxide is used as a binder, and may be selected from silicon dioxide ($SiO_2$) and/or aluminum oxide ($Al_2SiO_3$). In the catalyst, the clay is used as a matrix (i.e., carrier) and may be selected from kaolin and/or halloysite.

According to the present application, conventional reaction conditions may be employed for the catalytic conversion reaction of step 1) and the catalytic cracking reaction of step 3), and those skilled in the art may adjust the reaction conditions according to the difference of the reactors. For example, the reaction conditions of the catalytic conversion reaction of step 1), the catalytic cracking reaction of step 3), and/or into other catalytic conversion device(s) may include: a reaction temperature of about 420-750° C., a weight hourly space velocity of about 0.1-800 $h^{-1}$, a weight ratio of catalyst to feedstock of about 1:1 to about 150:1, a steam-to-feedstock weight ratio of about 0.03:1 to about 1:1.

In a preferred embodiment, the catalytic conversion reaction of step 1) and/or the catalytic cracking reaction of step 3) is carried out in a fluidized bed reactor under conditions including: a reaction temperature of about 420-650° C., a reaction time of about 0.05-20 seconds, and a weight ratio of the mesoporous zeolite-containing catalyst to feedstock of about 3:1 to about 15:1, and a steam-to-feedstock weight ratio of about 0.03:1 to about 0.5:1. Further preferably, the reaction conditions include: a reaction temperature of about 480-600° C., a reaction time of about 0.1-15 seconds, and a weight ratio of the mesoporous zeolite-containing catalyst to feedstock of about 4:1 to about 12:1, and a steam-to-feedstock weight ratio of about 0.05:1 to about 0.3:1.

In a further preferred embodiment, said catalytic conversion reaction of step 1) is carried out until a gaseous product is obtained that has one or more of the following characteristics: a mass fraction ratio of liquefied gas ($C_3$ and $C_4$) to dry gas ($C_2$ or lower) of not less than about 7, preferably not less than about 10; a methane yield of no greater than about 2.0%, preferably no greater than about 1.0%; a mass fraction ratio of propylene to propane in the liquefied gas of not less than about 3.5, preferably not less than about 5.0; and a mass fraction ratio of isobutylene to isobutane of not less than about 1.5, preferably not less than about 4.0. The inventors of the present application have found that in this further preferred embodiment, the catalytic conversion reaction of step 1) is capable of achieving a high olefin yield (e.g., $C_2$-$C_{12}$ olefins) and a low alkane yield (e.g., $C_1$-$C_{12}$ alkanes), and therefore is favorable to the improvement of the propylene yield of the process according to the present application.

In a further preferred embodiment, the catalytic conversion reaction of step 1) and/or the catalytic cracking reaction of step 3) are carried out in a diameter-transformed riser reactor comprising, from bottom to top, a first reaction zone in which a cracking reaction of macromolecules is mainly carried out and a second reaction zone having a diameter larger than that of the first reaction zone in which cracking, hydrogen transfer and isomerization reactions are mainly carried out, and the reaction conditions in the first reaction zone include: a reaction temperature of about 510-650° C., a reaction time of about 0.05-1.0 second, and a catalyst-to-feedstock weight ratio of about 3:1 to about 15:1, a steam-to-feedstock weight ratio of about 0.03:1 to about 0.3:1, and a pressure of about 130-450 KPa; the reaction conditions in the second reaction zone include: a reaction temperature of about 420-550° C., and a reaction time of about 1.5-20 seconds. Further preferably, the reaction conditions in the first reaction zone include: a reaction temperature of about 520-600° C., a reaction time of about 0.1-1 second, preferably about 0.1-0.5 second, and a catalyst-to-feedstock weight ratio of about 4:1 to about 12:1, a steam-to-feedstock weight ratio of about 0.05:1 to about 0.2:1; the reaction conditions in the second reaction zone include: a reaction temperature of about 460-530° C. and a reaction time of about 2-10 seconds.

According to the present application, in order to increase the catalyst-to-oil ratio in the downstream part of the catalytic conversion reaction device and to improve the cracking activity of the catalyst, hot or cold regenerated catalyst, semi-regenerated catalyst, spent catalyst or fresh catalyst may be supplemented to the middle of the catalytic conversion reaction device, such as the bottom of the second reaction zone. The cooled regenerated catalyst and the cooled semi-regenerated catalyst are obtained by cooling the resultant obtained after a two-stage regeneration and an one-stage regeneration of the spent catalyst, respectively, wherein the regenerated catalyst has a carbon content of less than about 0.1 wt %, preferably less than about 0.05 wt %, and the semi-regenerated catalyst has a carbon content of about 0.1-0.9 wt %, preferably about 0.15-0.7 wt %; and the spent catalyst has a carbon content of about 0.9 wt % or more, preferably about 0.9-1.2 wt %.

In some preferred embodiments, the separation step 2a) may comprise;
- a1) separating from the catalytic conversion product obtained in step 1) as the starting material a fraction having a distillation range <145° C., a fraction having a distillation range of about 145-260° C., a fraction having a distillation range >260° C., optionally a propylene product and optionally a fraction comprising $C_4$ olefin; and
- a2) separating the first propylene precursor that comprises $C_6$ olefin from the resulting fraction having a distillation range <145° C., and/or one or more of the following fractions: a fraction comprising $C_5$ olefin, a fraction comprising $C_7$ olefin and a fraction comprising $C_8$ olefin.

In a further preferred embodiment, the separation step 2a) may further comprise one or more of the following:
- a3) separating n-paraffins and isoparaffins from the fraction having a distillation range <145° C., and recycling the n-paraffins and isoparaffins to the catalytic conversion reaction in step 1) or sending them to other reaction device(s);
- a4) recycling the fraction having a distillation range of about 145-260° C. to the catalytic conversion reaction in step 1) or sending it to other reaction device(s); and
- a5) subjecting the fraction having a distillation range >260° C. to a hydrotreatment and then recycling it to the catalytic conversion reaction in step 1) or sending it to other reaction device(s).

Preferably, the hydrotreatment is carried out in the presence of a hydrotreating catalyst and under conditions including: a hydrogen partial pressure of about 3.0-20.0 MPa, a reaction temperature of about 300-450° C., a hydrogen-to-oil volume ratio of about 300-2000, and a volume space velocity of about 0.1-3.0 $h^{-1}$; wherein the hydrotreating catalyst comprises a carrier, a metallic component supported on the carrier, and optionally an additive, wherein the carrier is selected from alumina, amorphous silica-alumina or a combination thereof, the metallic component is selected from a Group VIB metal, a Group VIII metal or a combination thereof, the additive is one or more selected from the group consisting of fluorine, phosphorus, titanium and platinum, the Group VIB metal is selected from Mo, W or a combination thereof, and the Group VIII metal is selected from Co, Ni or a combination thereof; the additive is present in an amount of about 0-10 wt %, the Group VIB metal is present in an amount of about 12-39 wt %, and the Group VIII metal is present in an amount of about 1-9 wt %, based on the weight of the hydrotreating catalyst.

According to the present application, the catalytic conversion product may be separated into dry gas, propane, propylene, BTX, etc. in addition to the above-mentioned fractions, and the separation of the various fractions, aromatic hydrocarbons and olefins, may be carried out by methods well known to those skilled in the art. Methods for separation of the $C_4$ olefin-containing fraction, the $C_5$ olefin-containing fraction, the $C_7$ olefin-containing fraction, and the $C_8$ olefin-containing fraction are well known to those skilled in the art, of which the detailed description is omitted herein for brevity. In addition, since catalysts are susceptible to be poisoned by dienes, and an excessively high level of sulfur, especially mercaptan and hydrogen sulfide, may reduce the activity of the oligomerization catalyst and promote the formation of resin in the oligomerization gasoline, each fraction comprising olefins can be treated by a pre-treatment unit, such as, for removing dienes by selective hydrogenation, for desulfurization using ethanolamine, for alkali washing and water washing, and for removing basic nitride compounds, and then subjected to oligomerization. The above-mentioned treatments are well known to those skilled in the art, of which the detailed description is omitted herein for brevity.

In a particularly preferred embodiment, the present application provides a process for producing propylene in a high yield, comprising the steps of:
1) injecting a hydrocarbon feedstock into a catalytic conversion reactor to contact with a catalytic conversion catalyst for catalytic conversion reaction to obtain a catalytic conversion product;
2) subjecting the resulting reaction product to one or more of the following operations:
   (i) separating therefrom at least a fraction comprising $C_4$ olefin, introducing the fraction comprising $C_4$ olefin and/or an external fraction comprising $C_4$ olefin into an oligomerization reactor to contact with an oligomerization catalyst for oligomerization reaction to obtain an oligomerization product comprising $C_{12}$ olefin;
   (ii) separating therefrom at least a fraction comprising $C_5$ olefin and a fraction comprising $C_7$ olefin, introducing the fraction comprising $C_5$ olefin and the fraction comprising $C_7$ olefin, and/or an external fraction comprising $C_5$ olefin and an external fraction comprising $C_7$ olefin into an oligomerization reactor to contact with an oligomerization catalyst for oligomerization reaction to obtain an oligomerization product comprising $C_{12}$ olefin;
   (iii) separating therefrom at least a fraction comprising $C_4$ olefin and a fraction comprising $C_8$ olefin, introducing the fraction comprising $C_4$ olefin and the fraction comprising $C_8$ olefin, and/or an external fraction comprising $C_4$ olefin and an external fraction comprising $C_8$ olefin into an oligomerization reactor to contact with an oligomerization catalyst for oligomerization reaction to obtain an oligomerization product comprising $C_{12}$ olefin;
   separating $C_{12}$ olefin from the resulting oligomerization product and introducing the resulting $C_{12}$ olefin into the catalytic conversion reaction device (preferably at the middle or bottom) for catalytic conversion and/or into other catalytic conversion device(s).

According to the present application, the resulting oligomerization product can be passed to a filtering device to remove carried catalyst powder, and then introduced into a catalytic conversion reaction device for further reaction. The $C_{12}$ olefin introduced into the catalytic conversion reaction device and/or other catalytic conversion device(s) may account for about 1 wt % to about 90 wt %, preferably about 1 wt % to about 40 wt %, of the catalytic conversion feedstock, including all fresh hydrocarbon feedstocks and recycled streams, such as recycled $C_{12}$ olefin, introduced into the catalytic conversion reaction device and other catalytic conversion device(s).

In a further preferred embodiment, the process may further comprise: separating a fraction comprising $C_6$ olefin from the catalytic conversion product, introducing the resulting fraction comprising $C_6$ olefin into the catalytic conversion reaction device for catalytic conversion reaction and/or into other catalytic conversion device(s); wherein the $C_6$ olefin introduced into the catalytic conversion reaction device for catalytic conversion and/or other catalytic conversion device(s) accounts for about 1 wt % to about 30 wt % of the catalytic conversion feedstock.

In a further preferred embodiment, the process may further comprise: separating a fraction having a distillation range <145° C. from the resulting catalytic conversion product, separating n-paraffins and isoparaffins from the resulting fraction having a distillation range <145° C., and recycling the resulting n-paraffins and isoparaffins to the catalytic conversion reaction device and/or to other catalytic conversion device(s), thereby improving the utilization rate of this fraction.

In a further preferred embodiment, the process may further comprise: separating a fraction having a distillation range of 145-260° C. from the resulting catalytic conversion product, and introducing the resulting fraction having a distillation range of 145-260° C. into the catalytic conversion reaction device (preferably at the bottom) and/or into other catalytic conversion device(s), thereby improving the utilization rate of this fraction.

In a further preferred embodiment, the process may further comprise: separating a fraction having a distillation range >260° C. from the resulting catalytic conversion product, contacting the resulting fraction having a distillation range >260° C. with a hydrotreating catalyst for a hydrotreatment, and using the resulting hydrogenation product as a catalytic conversion feedstock.

In a second aspect, the present application provides a system for producing propylene, comprising a pretreatment unit configured to pretreat a starting material comprising olefin(s) having 4 or more carbon atoms, to obtain a propylene precursor comprising olefin(s) having $3\times2^n$ carbon atoms, wherein n is an integer greater than or equal to 1, preferably 1 to 3, more preferably 1 to 2, and a reaction unit configured to catalytically crack the propylene precursor to obtain a reaction product comprising propylene,
wherein the pretreatment unit comprises at least one of a first separation unit configured to separate the starting material to obtain a first propylene precursor comprising olefin(s) having $3\times2^n$ carbon atoms, and/or one or more of the following fractions: a fraction comprising $C_4$ olefin, a fraction comprising $C_5$ olefin, a fraction comprising $C_7$ olefin, and a fraction comprising $C_8$ olefin; and an oligomerization unit configured to carry out an olefin oligomerization reaction on the starting material or a fraction thereof, and optionally separate the resulting oligomerization product, to obtain a second propylene precursor comprising olefin(s) having $3\times2^m$ carbon atoms, wherein m is an integer greater than or equal to 2, preferably 2 to 3.

In a preferred embodiment, the pretreatment unit comprises a first separation unit and an oligomerization unit,
wherein the first separation unit is configured to separate the starting material to obtain one or more of the following fractions: a fraction comprising $C_4$ olefin, a fraction comprising $C_5$ olefin, a fraction comprising $C_7$ olefin and a fraction comprising $C_8$ olefin, and optionally a first propylene precursor comprising $C_6$ olefin; and
the oligomerization unit is configured to carry out an olefin oligomerization reaction on the fraction comprising $C_4$ olefin, an oligomerization feedstock obtained by combining the fraction comprising $C_5$ olefin with the fraction comprising $C_7$ olefin, and/or an oligomerization feedstock obtained by combining the fraction comprising $C_4$ olefin with the fraction comprising $C_8$ olefin, respectively, and optionally separating the resulting oligomerization product, to obtain the second propylene precursor that comprises $C_{12}$ olefin.

In a preferred embodiment, the reaction unit comprises a catalytic conversion reaction device, an oil-catalyst separation device and a regenerator,
wherein the catalytic conversion reaction device is configured to perform a catalytic conversion reaction on a hydrocarbon feedstock in the presence of a catalyst to obtain a reaction effluent comprising a catalytic conversion product and a spent catalyst, wherein the catalytic conversion product comprises olefin(s) having 4 or more carbon atoms and optionally propylene,
the oil-catalyst separation device is configured to separate the catalytic conversion product from the spent catalyst in the reaction effluent, and transport the catalytic conversion product to the pretreatment unit to serve as the starting material;
the regenerator is configured to regenerate the spent catalyst and recycle the regenerated catalyst to the catalytic conversion reaction device; and
the pretreatment unit is configured to pretreat the starting material to obtain the propylene precursor comprising olefin(s) having $3\times2^n$ carbon atoms and optionally a propylene product, and recycle the propylene precursor to the catalytic conversion reaction device.

In a preferred embodiment, the pretreatment unit comprises a first separation unit comprising a product separation unit and an olefin separation device, and an oligomerization unit comprising at least one oligomerization reactor and at least one rectifying column,
wherein the product separation unit is configured to fractionate the catalytic conversion product comprising olefin(s) having 4 or more carbon atoms and optionally propylene serving as the starting material to obtain a fraction having a distillation range <145° C., optionally a propylene product and optionally a fraction comprising $C_4$ olefin,
the olefin separation device is configured to separate the fraction having a distillation range <145° C. to obtain one or more of the following fractions: a fraction comprising $C_5$ olefin, a fraction comprising $C_7$ olefin and a fraction comprising $C_8$ olefin, and optionally a first propylene precursor comprising $C_6$ olefin,
the one or more oligomerization reactors are configured to carry out an olefin oligomerization reaction on the fraction comprising $C_4$ olefin, an oligomerization feedstock obtained by combining the fraction comprising $C_5$ olefin with the fraction comprising $C_7$ olefin and/or an oligomerization feedstock obtained by combining the fraction comprising $C_4$ olefin with the fraction comprising $C_8$ olefin, respectively, to obtain an oligomerization product comprising $C_{12}$ olefin, the one or more rectifying columns are configured to separately separate the oligomerization products from the one or more oligomerization reactors to obtain the second propylene precursor that comprises $C_{12}$ olefin.

In a particularly preferred embodiment, the system of the present application comprises a catalytic conversion reactor, an oil-catalyst separation device, a regenerator, a product separation unit, an olefin separation device, an oligomerization reactor, a rectifying column, and optionally other catalytic conversion device(s);

the catalytic conversion reactor is provided with a feedstock oil inlet, a catalyst inlet, an oil-catalyst outlet and a $C_{12}$ olefin inlet, the oil-catalyst separation device is provided with an oil-catalyst inlet, a catalyst outlet and a reaction product outlet, the regenerator is provided with a catalyst inlet and a catalyst outlet, the product separation unit is provided with a reaction product inlet and at least one fraction outlet, the olefin separation device is provided with a fraction inlet and at least one olefin outlet, the oligomerization reactor is provided with a feedstock inlet and an oligomerization product outlet, the rectifying column is provided with an oligomerization product inlet, a $C_{12}$ olefin outlet and a separated product outlet, and said other catalytic conversion device(s) is provided with a feedstock oil inlet, a catalyst inlet and an oil-catalyst outlet; the oil-catalyst outlet of the catalytic conversion reactor is in fluid communication with the oil-catalyst inlet of the oil-catalyst separating device, the catalyst inlet of the catalytic conversion reactor is in fluid communication with the catalyst outlet of the regenerator, the catalyst inlet of the regenerator is in fluid communication with the catalyst outlet of the oil-catalyst separation device, the reaction product outlet of the oil-catalyst separation device is in fluid communication with the reaction product inlet of the product separation unit, at least one fraction outlet of the product separation unit is in fluid communication with the fraction inlet of the olefin separation device, the olefin outlet of the olefin separation device is in fluid communication with the feedstock inlet of the oligomerization reactor, the oligomerization product outlet of the oligomerization reactor is in fluid communication with the oil-gas inlet of the rectifying column, the $C_{12}$ olefin outlet of the rectifying column is in fluid communication with the $C_{12}$ olefin inlet of the catalytic conversion reactor and/or the feedstock oil inlet of said other catalytic conversion device(s);

the system is further configured in one, two or three of the following ways (a)-(c):
(a) the product separation unit is further provided with a $C_4$ fraction outlet, the $C_4$ fraction outlet of the product separation unit is in fluid communication with the feedstock inlet of the oligomerization reactor;
(b) the olefin separation device is at least provided with a $C_5$ olefin outlet and a $C_7$ olefin outlet, and the $C_5$ olefin outlet and $C_7$ olefin outlet of the olefin separation device are in fluid communication with the feedstock inlet of the oligomerization reactor;
(c) the olefin separation device is at least provided with a $C_8$ olefin outlet, and the product separation unit is further provided with a $C_4$ fraction outlet, the $C_8$ olefin outlet of the olefin separation device and the $C_4$ fraction outlet of the product separation unit being in fluid communication with the feedstock inlet of the oligomerization reactor.

In a further preferred embodiment, when the product separation unit, the olefin separation device and the oligomerization reactor are configured in two or more of the ways (a) to (c), one or more oligomerization reactors, preferably a plurality of oligomerization reactor, may be provided. For example, for each of the ways (a) to (c), an oligomerization reactor is provided to perform oligomerization separately.

In a further preferred embodiment, when the reactor is a diameter-transformed riser reactor comprising two reaction zones, the olefin separation device may further be provided with a $C_6$ olefin outlet, and the $C_6$ olefin outlet may be in fluid communication with the feedstock inlet of the second reaction zone of the diameter-transformed riser reactor. Further preferably, the product separation unit can be further provided with a 145-260° C. fraction outlet, and the 145-260° C. fraction outlet can be in fluid communication with the feedstock inlet of the first reaction zone of the diameter-transformed riser reactor.

In a further preferred embodiment, the system may further comprise a hydrotreating reactor, the hydrotreating reactor may be provided with a feedstock inlet and a product outlet, the product separation unit may further be provided with a >260° C. fraction outlet, the >260° C. fraction outlet may be in fluid communication with the feedstock inlet of the hydrotreating reactor, and the product outlet of the hydrotreating reactor may be in fluid communication with the feedstock inlet of the second reaction zone of the diameter-transformed riser reactor.

The process of the present application will be further illustrated with reference to the drawings, but is not limited thereto.

First Type of Embodiments

As shown in FIG. 1, a pre-lifting medium is injected into the bottom of a diameter-transformed riser reactor 2 through pipeline 1, a regenerated catalytic conversion catalyst from pipeline 16 moves upwards along the riser reactor 2 under the action of the pre-lifting medium, a preheated feedstock oil is injected into the bottom of a first reaction zone I of the riser reactor 2 through pipeline 3 together with an atomizing steam from pipeline 4, and mixed with the process stream in the riser reactor 2, and then the feedstock oil undergoes a reaction on the hot catalyst and moves upwards. A light feedstock oil is injected into the bottom of the second reaction zone II of the riser reactor 2 through pipeline 5 together with an atomizing steam from pipeline 6, and mixed with the oil-catalyst stream in the riser reactor, and then the light feedstock oil undergoes a reaction on the catalyst containing a certain amount of carbon and moves upwards. The reaction product generated and the inactivated spent catalyst are passed to a cyclone separator in a disengager 8 through an outlet section 7 to perform the separation of the spent catalyst and the reaction product, the reaction product is passed to a gas collection chamber 9, and catalyst fine powder is returned to the disengager through a dipleg. The spent catalyst in the disengager flows to a stripping section 10 where it is contacted with steam from pipeline 11. Oil gas stripped from the spent catalyst is passed to the gas collection chamber 9 after passing through the cyclone separator. The stripped spent catalyst is passed to a regenerator 13 via standpipe 12, main air is introduced into the regenerator through pipeline 14 to burn off the coke on the spent catalyst so as to regenerate the inactivated spent catalyst. The resulting flue gas is passed to a flue gas expander (not shown in the figure) through pipeline 15, and the regenerated catalyst is injected into the bottom of the riser reactor via pipeline 16.

Oil gas in the gas collection chamber 9 is passed to a subsequent product separation unit 18 through vapor line 17, dry gas obtained by separation is withdrawn through pipeline 19, ethylene is withdrawn through pipeline 20, propylene is withdrawn through pipeline 21, propane is withdrawn through pipeline 22, $C_4$ olefin is withdrawn through pipeline 23, butane is withdrawn through pipeline 24, a fraction having a distillation range <145° C. is introduced into an olefin separation device 31 through pipeline 25, a fraction having a distillation range of 145-260° C. is withdrawn through pipeline 26, or is introduced into the first reaction zone I for reuse, a fraction having a distillation range >260° C. is withdrawn through pipeline 27, or is passed to a hydrotreating reactor 54. Light components separated from the hydrotreating reactor are withdrawn through pipeline 55, and a hydrogenated product is recycled to the second reaction zone II through pipeline 56 to further produce the propylene. The fraction <145° C. is passed to an olefin separation device 31 for separation, $C_5$ olefin obtained is withdrawn via pipeline 32, $C_6$ olefin obtained is withdrawn via pipeline 33, $C_7$ olefin obtained is withdrawn via pipeline 34, $C_8$ olefin obtained is withdrawn via pipeline 35, BTX obtained is withdrawn via pipeline 36 and n-/iso-paraffins obtained are withdrawn via pipeline 37.

$C_4$ olefin is introduced into oligomerization reactors 41 and 42 via pipeline 23, $C_5$ olefin is introduced into an oligomerization reactor 43 via pipeline 32, $C_7$ olefin is introduced into an oligomerization reactor 43 via pipeline 34, and $C_8$ olefin is introduced into an oligomerization reactor 42 via pipeline 35.

In the oligomerization reactor 41, $C_4$ olefin is subjected to an oligomerization reaction to obtain an oligomerization product comprising $C_{12}$ olefin, which is then passed to a rectifying column 51 to separate $C_{12}$ olefin. The $C_{12}$ olefin obtained is introduced into the catalytic conversion reaction device and/or into other catalytic conversion device(s) through pipeline 38 for further production of propylene. In the oligomerization reactor 42, $C_4$ olefin and $C_8$ olefin are subjected to an oligomerization reaction to obtain an oligomerization product comprising $C_{12}$ olefin, which is then passed to a rectifying column 52 to separate $C_{12}$ olefin. The $C_{12}$ olefin obtained is introduced into the catalytic conversion reaction device and/or into other catalytic conversion device(s) through pipeline 38 for further production of propylene. In the oligomerization reactor 43, $C_5$ olefin and $C_7$ olefin are subjected to an oligomerization reaction to obtain an oligomerization product comprising $C_{12}$ olefin, which is then passed to a rectifying column 53 to separate $C_{12}$ olefin. The $C_{12}$ olefin obtained is introduced into the catalytic conversion reaction device and/or into other catalytic conversion device(s) for further production of propylene; $C_6$ olefin is introduced into the second reaction zone II via pipeline 33 for further production of propylene.

Second Type of Embodiments

Figure 2:
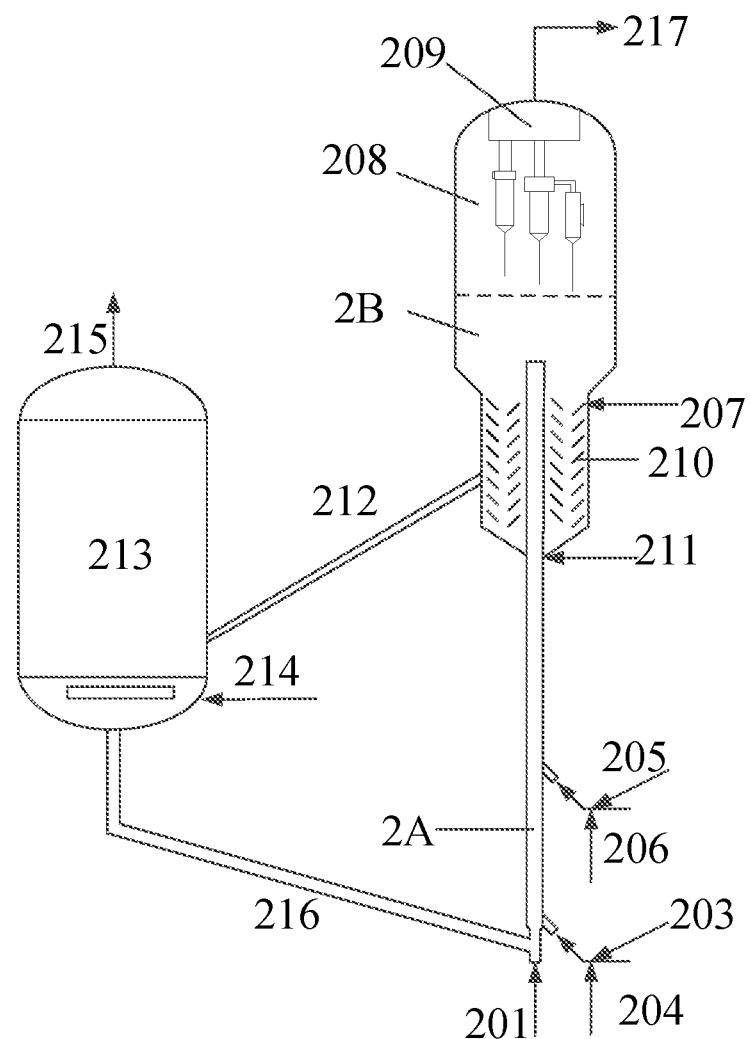
FIG. 2 is a schematic diagram of a second embodiment of the process and system of the present application.

A preferred technical solution of this type of embodiments comprises the following steps:

As shown in FIG. 2, a hot regenerated catalyst from pipeline 216 moves upwards along the riser unit 2A under the action of a pre-lifting steam from pipeline 201, a feedstock oil from pipeline 203 is atomized by an atomizing steam from pipeline 204 and introduced into the riser unit 2A to contact with the process stream in the riser unit 2A, and subjected to a catalytic conversion reaction at a reaction temperature of about 500-650° C., a reaction time of about 0.5-4 seconds, a reaction pressure of about 0.15-0.30 MPa (absolute), and a weight ratio of catalytic conversion catalyst to feedstock of about 1-100. Optionally, a light feedstock (e.g., diesel oil, propane) from pipeline 205 is atomized by an atomizing steam from pipeline 206 and fed into the riser unit 2A; the reaction stream obtained in the riser unit 2A is passed to a dense phase bed unit 2B for further catalytic conversion reaction at a reaction temperature of about 480-620° C., a weight hourly space velocity of about 0.2-30 $h^{-1}$ and a reaction pressure of about 0.15-0.30 MPa (absolute) to obtain a spent catalyst and a reaction product. The spent catalyst and the reaction product are separated in a disengager 208, the reaction product is passed to a gas collection chamber 209 and withdrawn through vapor line 217. The spent catalyst is passed to a stripping section 210 for countercurrent stripping with a stripping steam from pipeline 211, the stripped spent catalyst is passed to a regenerator 213 via standpipe 212 for regeneration by burning off the coke with air from pipeline 214. The resulting flue gas is discharged from the regenerator 213 from pipeline 215, and the regenerated catalyst is recycled to the riser unit 2A through pipeline 216 as the catalytic conversion catalyst. The reaction product is separated to obtain at least $C_4$, $C_5$, $C_7$ and $C_8$ olefin fractions, which are subjected to oligomerization and separation to produce $C_{12}$ olefin. The $C_{12}$ olefin obtained is introduced via pipeline 207 into the dense phase bed unit 2B for further cracking to increase propylene yield. Optionally, a $C_6$ olefin fraction is further separated from the reaction product and introduced into the dense phase bed unit 2B for further cracking to increase propylene yield.

Third Type of Embodiments

Figure 3:
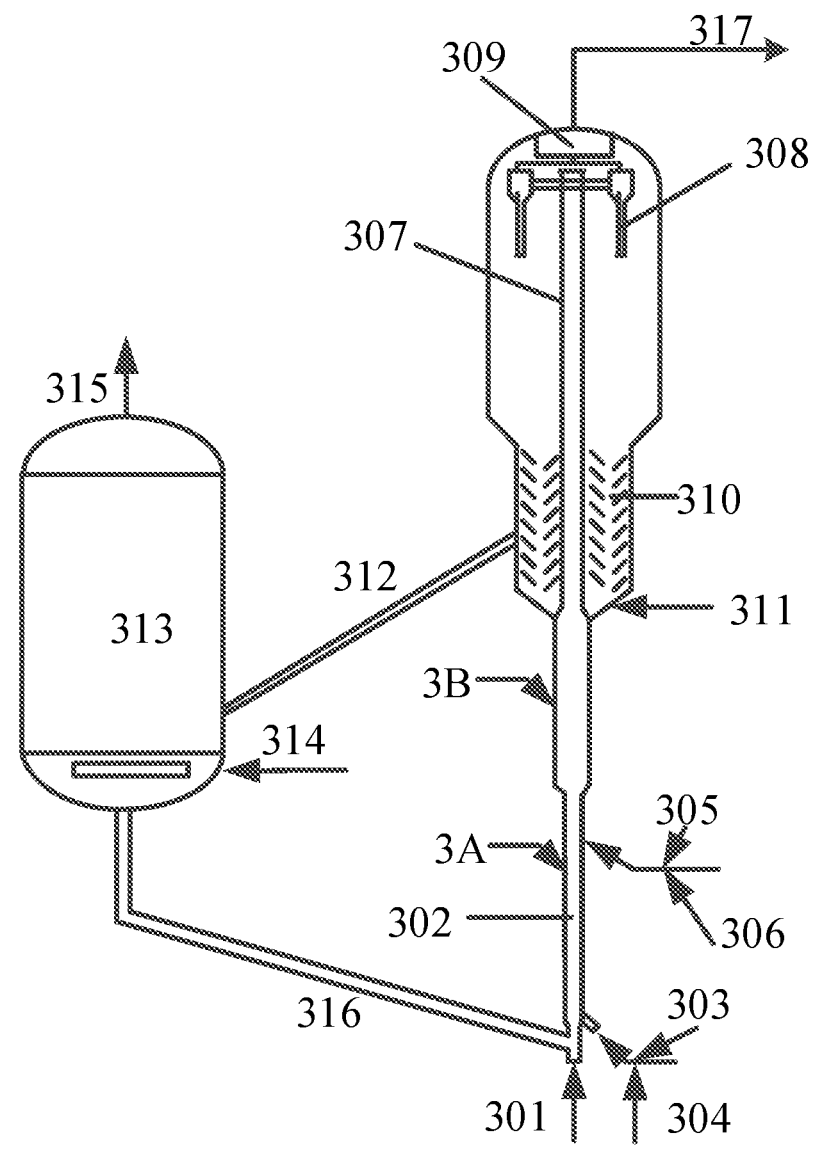
FIG. 3 is a schematic diagram of a third embodiment of the process and system of the present application.

A preferred technical solution of this type of embodiment comprises the following steps:

As shown in FIG. 3, a hot regenerated catalyst from pipeline 316 moves upwards along a first reaction zone 3A of a diameter-transformed riser reactor 302 under the action of a pre-lifting medium from pipeline 301, a feedstock oil from pipeline 303 is atomized by an atomizing steam from pipeline 304 and introduced into the first reaction zone 3A to contact with the process stream in the first reaction zone 3A, and subjected to a catalytic conversion reaction first in the first reaction zone 3A and then in a second reaction zone 3B, wherein the reaction conditions in the first reaction zone 3A include: a reaction temperature of about 520-600° C., a reaction time of about 0.1-1 second, and a catalyst-to-feedstock weight ratio of about 4:1 to about 12:1, a steam-to-feedstock weight ratio of about 0.05:1 to about 0.2:1; and the reaction conditions in the second reaction zone 3B include: a reaction temperature of about 460-530° C. and a reaction time of about 2-10 seconds. The resulting reaction product and coked spent catalyst are passed from an outlet section 307 of the riser reactor to a disengager 308 for separation, the reaction product is passed to a gas collection chamber 309 and withdrawn through vapor line 317, the spent catalyst is passed to a stripping section 310 for countercurrent stripping with a stripping steam from pipeline 311. The stripped spent catalyst is introduced into a regenerator 313 via standpipe 312 for regeneration by burning off the coke with air from pipeline 314, the resulting flue gas is discharged from the regenerator 313 via pipeline 315, and the regenerated catalyst is recycled to the diameter-transformed riser reactor 302 through pipeline 316 as the catalytic conversion catalyst. The reaction product is separated to obtain at least $C_4$, $C_5$, $C_7$ and $C_8$ olefin fractions, which are subjected to oligomerization and separation to produce $C_{12}$ olefin. The $C_{12}$ olefin obtained is atomized by an atomizing steam from pipeline 306 and then introduced via pipeline 305 into the second reaction zone 3B and/or into other catalytic conversion device(s) for further cracking to increase propylene yield. Optionally, a $C_6$ olefin fraction is further separated from the reaction product and introduced into the second reaction zone 3B for further cracking to increase propylene yield.

Fourth Type of Embodiments

A preferred technical solution of this type of embodiments comprises the following steps:

A feedstock oil is introduced into the bottom of a first riser reactor 4A through pipeline 403, a hot regenerated catalyst from pipeline 415 is contacted with the feedstock oil after being lifted by a pre-lifting steam from pipeline 401, and a reaction is carried out under conditions including a reaction temperature of about 450-600° C., a reaction time of about 0.5-5 seconds, a reaction pressure of about 0.15-0.40 MPa (absolute), and a weight ratio of catalytic conversion catalyst to feedstock of about 5-20. Optionally, a light feedstock (such as diesel oil and propane) from pipeline 404 is introduced into the first riser reactor 4A for reaction, the resulting spent catalyst and reaction product are passed to a disengager 408 along an outlet section 407 for oil-catalyst separation. The resulting reaction product is passed to a gas collection chamber 409 and withdrawn through vapor line 410, the spent catalyst is passed to a stripping section 406 for countercurrent stripping with a stripping steam from pipeline 405, and then introduced into a regenerator 412 via standpipe 411 for regeneration by burning off the coke with air from pipeline 413. The resulting flue gas is discharged from the regenerator 412 through pipeline 414, the regenerated catalyst is recycled to said first riser reactor 4A through pipeline 415 as the catalytic conversion catalyst. The reaction product from the first riser reactor 4A is separated to obtain at least a $C_4$ olefin-containing fraction and an olefin-rich gasoline fraction. The $C_4$ olefin is subjected to oligomerization and separation to produce a $C_{12}$ olefin-containing fraction, which is introduced through pipeline 431 into a middle part of a second riser reactor 4B, and the olefin-rich gasoline fraction is introduced into a bottom part of the second riser reactor 4B through pipeline 423. A hot regenerated catalyst from pipeline 416 is, after being lifted by a pre-lifting steam from pipeline 421, contacted with the olefin-rich gasoline fraction and the $C_{12}$ olefin-containing fraction sequentially, to conduct further cracking under conditions including a reaction temperature of about 350-660° C., a reaction time of about 1.0-8 seconds, a reaction pressure of about 0.15-0.40 MPa (absolute), and a weight ratio of catalytic conversion catalyst to feedstock of about 3-45, to increase propylene yield. The resulting reaction effluent is passed to a disengager 428 along an outlet section 427 for oil-catalyst separation, the resulting reaction product is passed to a gas collection chamber 429 and withdrawn through vapor line 430, the spent catalyst is passed to a stripping section 426 for countercurrent stripping with a stripping steam from pipeline 425 and then is introduced into a regenerator 412 via standpipe 417 for regeneration by burning off the coke with air from pipeline 413. The resulting flue gas is discharged from the regenerator 412 via pipeline 414. Optionally, a fraction comprising $C_6$ olefin is further separated from the reaction product obtained from the first riser reactor 4A and introduced into a middle part of the second riser reactor 4B for further cracking to increase propylene yield.

In particularly preferred embodiments, the present application provides the following technical solutions:

1. A catalytic conversion process for producing propylene in high yield, comprising the steps of:
    injecting a hydrocarbon feedstock into a catalytic conversion reactor to contact with a catalytic conversion catalyst for catalytic conversion reaction to obtain a reaction product and a spent catalyst;
    introducing the resulting spent catalyst into a regenerator for regeneration by coke-burning to obtain a, and recycling the regenerated catalyst to the catalytic conversion reactor as the catalytic conversion catalyst;
    subjecting the resulting reaction product to one, two or three of the following operations:
    (i) separating therefrom at least a fraction comprising $C_4$ olefin, introducing the fraction comprising $C_4$ olefin and/or an external fraction comprising $C_4$ olefin into an oligomerization reactor to contact with an oligomerization catalyst for oligomerization reaction to obtain an oligomerization product comprising $C_{12}$ olefin;
    (ii) separating therefrom at least a fraction comprising $C_5$ olefin and a fraction comprising $C_7$ olefin, introducing the fraction comprising $C_5$ olefin and the fraction comprising $C_7$ olefin, and/or an external fraction comprising $C_5$ olefin and an external fraction comprising $C_7$ olefin into an oligomerization reactor to contact with an oligomerization catalyst for oligomerization reaction to obtain an oligomerization product comprising $C_{12}$ olefin;
    (iii) separating therefrom at least a fraction comprising $C_4$ olefin and a fraction comprising $C_8$ olefin, introducing the fraction comprising $C_4$ olefin and the fraction comprising $C_8$ olefin, and/or an external fraction comprising $C_4$ olefin and an external fraction comprising $C_8$ olefin into an oligomerization reactor to contact with an oligomerization catalyst for oligomerization reaction to obtain an oligomerization product comprising $C_{12}$ olefin;
    separating $C_{12}$ olefin from the resulting oligomerization product, and introducing the resulting $C_{12}$ olefin into the catalytic conversion reactor for catalytic conversion and/or into other catalytic conversion device(s).

2. The process according to Item 1, further comprising: separating a fraction comprising $C_6$ olefin from the reaction product, introducing the fraction comprising $C_6$ olefin into the catalytic conversion reactor for catalytic conversion reaction and/or into other catalytic conversion device(s); wherein $C_6$ olefin introduced into the catalytic conversion reactor for catalytic conversion and/or into other catalytic conversion device(s) accounts for about 1-30 wt % of the feedstock.

3. The process according to Item 1, wherein the oligomerization conditions involved in operations (i)-(iii) each independently include: a temperature of about 50-550° C., a pressure of about 0.2-8.0 MPa, and a weight hourly space velocity of about 0.1-10 h$^{-1}$;
    in operation (ii), the weight ratio of $C_5$ olefin to $C_7$ olefin is about 1:0.7 to about 1:3;
    in operation (iii), the weight ratio of $C_4$ olefin to $C_8$ olefin is about 1:0.5 to about 1:3;
    the oligomerization catalysts involved in operations (i)-(iii) are each independently one or more selected from the group consisting of phosphoric acid catalysts, acidic resins, silica-alumina solid acid catalysts, and zeolite solid acid catalysts.

4. The process according to Item 3, wherein the phosphoric acid catalyst is one or more of a catalyst formed by loading phosphoric acid on diatomite, a catalyst formed by loading phosphoric acid on activated carbon, a catalyst formed by phosphoric acid-soaked quartz sand, a catalyst formed by loading phosphoric acid on silica gel, and a catalyst formed by loading copper pyrophosphate on silica gel;

the silica-alumina solid acid catalyst is a catalyst formed by loading metal ion(s) on alumina and/or an amorphous silica-alumina carrier, wherein the loaded metal ion(s) can be selected from Group VIII metals, Group IVA metals or a combination thereof;

the zeolite solid acid catalyst comprises about 10-100 wt % of a zeolite and about 0-90 wt % of a matrix based on the weight of the zeolite solid acid catalyst, wherein the zeolite is one or more of a Y-zeolite, a ZSM-5 zeolite, and a beta zeolite.

5. The process according to Item 1, wherein the oligomerization products obtained in operations (i)-(iii) may each has a $C_{12}$ olefin content of no less than about 40 wt %, more preferably no less than about 70 wt %, and most preferably no less than about 80 wt %, based on the weight of the oligomerization product.

6. The process according to Item 1, wherein the $C_4$ olefin content of the $C_4$ olefin-containing fraction is about 40-100 wt %, the $C_5$ olefin content of the $C_5$ olefin-containing fraction is about 40-100 wt %, the $C_7$ olefin content of the $C_7$ olefin-containing fraction is about 40-100 wt %, and the $C_8$ olefin content of the $C_8$ olefin-containing fraction is about 40-100 wt %;

the $C_4$ olefin-containing fraction has a sulfur content of no more than about 20 μg/g, a basic nitride content of no more than about 0.6 μg/g, a water content of about 600-1800 μg/g, and a diene content of no more than about 200 μg/g, based on the weight of the $C_4$ olefin-containing fraction;

the $C_5$ olefin-containing fraction has a sulfur content of no more than about 20 μg/g, a basic nitride content of no more than about 0.6 μg/g, a water content of about 600-1800 μg/g, and a diene content of no more than about 200 μg/g, based on the weight of the $C_5$ olefin-containing fraction;

the $C_7$ olefin-containing fraction has a sulfur content of no more than about 20 μg/g, a basic nitride content of no more than about 0.6 μg/g, a water content of about 600-1800 μg/g, and a diene content of no more than about 200 μg/g, based on the weight of the $C_7$ olefin-containing fraction;

the $C_8$ olefin-containing fraction has a sulfur content of no more than about 20 μg/g, a basic nitride content of no more than about 0.6 μg/g, a water content of about 600-1800 μg/g, and a diene content of no more than about 200 μg/g, based on the weight of the $C_8$ olefin-containing fraction.

7. A process according to Item 1, wherein the $C_{12}$ olefin introduced into the catalytic conversion reactor for catalytic conversion and/or into other catalytic conversion device(s) accounts for 1-90 wt %, such as 1-40 wt %, of the feedstock.

8. The process according to Item 1, wherein the feedstock is selected from the group consisting of petroleum hydrocarbons, other mineral oils, or combinations thereof, wherein the petroleum hydrocarbon is one or more selected from the group consisting of vacuum gas oil, atmospheric gas oil, coker gas oil, deasphalted oil, vacuum residue, atmospheric residue, and heavy aromatic raffinate oil; and said other mineral oil is one or more selected from coal liquefication oil, oil sand oil and shale oil.

9. The process according to Item 1, wherein the catalytic conversion catalyst comprises about 1-50 wt % of a zeolite, about 5-99 wt % of an inorganic oxide, and about 0-70 wt % of a clay, based on the weight of the catalytic conversion catalyst, wherein the zeolite is selected from the group consisting of mesoporous zeolites, macroporous zeolites, or a combination thereof, the mesoporous zeolite is selected from the group consisting of ZSM series zeolites, ZRP zeolites or a combination thereof, and the macroporous zeolite is one or more selected from the group consisting of REY zeolites, REHY zeolites, ultrastable Y zeolites and high-silica Y zeolites.

10. The process according to Item 1, wherein the catalytic conversion reactor and said other catalytic conversion device(s) are each independently selected from riser reactors, constant-linear-velocity fluidized beds, equal-diameter fluidized beds, upward transport beds, downer transport beds, or a combination of two or more thereof connected in series, wherein the riser reactor is an equal-diameter riser reactor or a diameter-transformed riser reactor;

11. The process according to Item 10, wherein the diameter-transformed riser reactor comprises two reaction zones, the reaction conditions in the first reaction zone include: a reaction temperature of about 510-650° C., a reaction time of about 0.05-1.0 second, a catalyst-to-feedstock weight ratio of about 3:1 to about 15:1, and a steam-to-feedstock weight ratio of about 0.03:1 to about 0.3:1; and the reaction conditions in the second reaction zone include: a reaction temperature of about 420-550° C., and a reaction time of about 1.5-20 seconds.

12. The process according to Item 11, wherein the diameter-transformed riser reactor comprises two reaction zones, the reaction conditions in the first reaction zone include: a reaction temperature of about 520-600° C., a reaction time of about 0.1-1 second, a catalyst-to-feedstock weight ratio of about 4:1 to about 12:1, and a steam-to-feedstock weight ratio of about 0.05:1 to about 0.2:1; and the reaction conditions in the second reaction zone include: a reaction temperature of about 460-530° C. and a reaction time of about 2-10 seconds.

13. The process according to Item 11, further comprising: separating the reaction product to obtain a fraction <145° C., a fraction of 145-260° C. and a fraction >260° C.;

separating n-paraffins and isoparaffins from the resulting fraction <145° C., and recycling the resulting n-paraffins and isoparaffins to the catalytic conversion reactor and/or other catalytic conversion device(s);

recycling the resulting fraction of 145-260° C. to the catalytic conversion reactor and/or other catalytic conversion device(s);

subjecting the resulting fraction having a distillation range >260° C. to a hydrotreatment, and then recycling the hydrotreated fraction to the catalytic conversion reactor and/or other catalytic conversion device(s), wherein the hydrotreatment is performed using a hydrotreating catalyst comprising a carrier, a metallic component supported on the carrier, and optionally an additive, wherein the carrier is selected from alumina, amorphous silica-alumina or a combination thereof, the metallic component is selected from Group VIB metal, Group VIII metal or a combination thereof, the additive is one or more selected from the group consisting of fluorine, phosphorus, titanium and platinum, the Group VIB metal is selected from Mo, W or a combination thereof, and the Group VIII metal is selected from Co, Ni or a combination thereof; and based on the weight of the hydrotreating catalyst, the additive is present in an amount of about 0-10 wt %, the Group VIB metal is present in an amount of about 12-39 wt %, and the Group VIII metal is present in an amount of about 1-9 wt %; the hydrotreating conditions include: a hydrogen partial pressure of about 3.0-20.0 MPa, a reaction temperature of about 300-450° C., a hydrogen-to-oil volume ratio of about 300-2000, and a volume space velocity of about 0.1-3.0.

14. A catalytic conversion system for producing propylene in high yield, comprising a catalytic conversion reactor, a regenerator, an oil-catalyst separation device, a product separation unit, an olefin separation device, an oligomerization reactor, a rectifying column and optionally other catalytic conversion device(s);

the catalytic conversion reactor is provided with a feedstock oil inlet, a catalyst inlet, an oil-catalyst outlet and a $C_{12}$ olefin inlet, the oil-catalyst separation device is provided with an oil-catalyst inlet, a catalyst outlet and a reaction product outlet, the olefin separation device is provided with a fraction inlet and an olefin outlet, said other catalytic conversion device(s) is provided with a feedstock oil inlet, a catalyst inlet and an oil-catalyst outlet, the regenerator is provided with a catalyst inlet and a catalyst outlet, the oligomerization reactor is provided with a feedstock inlet and an oligomerization product outlet, the rectifying column is provided with an oil-gas inlet, a $C_{12}$ olefin outlet and a separated product outlet, and the product separation unit is at least provided with a reaction product inlet; the oil-catalyst outlet of the catalytic conversion reactor is in fluid communication with the oil-catalyst inlet of the oil-catalyst separation device, the reaction product outlet of the oil-catalyst separation device is in fluid communication with the reaction product inlet of the product separation unit, the $C_{12}$ olefin outlet of the rectifying column is in fluid communication with the $C_{12}$ olefin inlet of the catalytic conversion reactor and/or the feedstock oil inlet of said other catalytic conversion device(s), the catalyst inlet of the catalytic conversion reactor is in fluid communication with the catalyst outlet of the regenerator, the catalyst inlet of the regenerator is in fluid communication with the catalyst outlet of the oil-catalyst separation device, the olefin outlet of the olefin separation device is in fluid communication with the feedstock inlet of the oligomerization reactor, and the oligomerization product outlet of the oligomerization reactor is in fluid communication with the oil-gas inlet of the rectifying column;

the system is further configured in one, two or three of the following ways (a)-(c):

(a) the product separation unit is further provided with at least a $C_4$ fraction outlet; the $C_4$ fraction outlet of the product separation unit is in fluid communication with the fraction inlet of the olefin separation device;

(b) the product separation unit is further provided with at least a $C_5$ fraction outlet and a $C_7$ fraction outlet, the $C_5$ fraction outlet and the $C_7$ fraction outlet of the product separation unit are in fluid communication with the fraction inlet of the olefin separation device;

(c) the product separation unit is further provided with at least a $C_4$ fraction outlet and a $C_8$ fraction outlet; the $C_4$ fraction outlet and the $C_8$ fraction outlet of the product separation unit are in fluid communication with the fraction inlet of the olefin separation device.

EXAMPLES

The present application will be further illustrated with reference to the following examples, but is not limited thereto.

The properties of the feedstocks A, B, C, D used in the examples are shown in Table 1.

TABLE 1

| Properties of the feedstocks used in the examples | | | | |
|---|---|---|---|---|
| Properties of the feedstocks | A | B | C | D |
| Density (20° C.)/(kg/m³) | 902 | 859.7 | 890.5 | 902.1 |
| Conradson carbon residue, wt % | 4.67 | 0.07 | 2.94 | 5.92 |
| C, wt % | 83.8 | 85.63 | 86.48 | 86.7 |
| H, wt % | 12.7 | 13.45 | 13.18 | 12.2 |
| S, wt % | 0.16 | 0.077 | 0.15 | 0.28 |
| N, wt % | 0.2109 | 0.058 | 0.19 | 0.38 |
| Fe, µg/g | 7.57 | 2.3 | 9.1 | 1.8 |
| Na, µg/g | — | 0.6 | 0.16 | 1.2 |
| Ni, µg/g | 5.04 | 4.9 | 5.4 | 3.3 |
| V, µg/g | 0.96 | 0.4 | 16.49 | 0.1 |
| Initial boiling point, ° C. | 221 | 316 | 261 | 263 |
| 10%, ° C. | 332 | 357 | 439 | 375 |
| 30%, ° C. | — | 390 | 501 | — |
| 50%, ° C. | 354 | 419 | 550 | 479 |

The preparation of the catalytic conversion catalyst A used in the examples is briefly described as follows:

1) 20 kg of $NH_4Cl$ was dissolved in 1000 kg of water, 100 kg (on a dry basis) of ZRP-1 zeolite as a crystallization product (available from Qilu Branch of Sinopec Catalyst Co., Ltd., $SiO_2/Al_2O_3=100$, rare earth content $RE_2O_3=2.0$ wt %) was added to the solution, exchanged at 90° C. for 0.5 hours, and filtered to obtain a filter cake; 4.0 g of $H_3PO_4$ (with a concentration of 85%) and 4.5 g of $Fe(NO_3)_3$ were added and dissolved in 90 g of water, and then mixed with the filter cake for impregnation, and dried; then calcined at 550° C. for 2 hours to obtain a mesoporous zeolite with MFI structure containing phosphorus and iron, of which the chemical composition determined by elemental analysis is as follows:

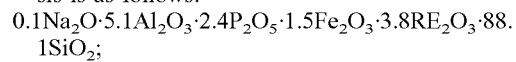

2) 75.4 kg of halloysite (an industrial product available from Suzhou China Clay Company, with a solid content of 71.6 wt %) was slurried with 250 kg of decationized water, then 54.8 kg of pseudo-boehmite (an industrial product available from Shandong Aluminum Plant, with a solid content of 63 wt %) was added, and the resultant was adjusted to a pH of 2-4 with hydrochloric acid, stirred uniformly, and allowed to stand for aging at 60-70° C. for 1 hour, kept at the pH of 2-4, and cooled to a temperature below 60° C., and then 41.5 kg of alumina sol (available from Qilu Branch of Sinopec Catalyst Co., Ltd., with an $Al_2O_3$ content of 21.7 wt %) was added, and stirred for 40 minutes to obtain a mixed slurry;

3) the phosphorus and iron-containing mesoporous zeolite with MFI structure (dry weight of 24.5 kg) obtained in step 1) was added into the mixed slurry obtained in step 2), stirred uniformly, spray dried, washed with ammonium dihydrogen phosphate solution (with a phosphorus content of 1 wt %) to remove free $Na^+$, and dried to obtain a catalytic conversion catalyst designated as Catalyst A. The catalyst comprises, on a dry basis, 20 wt % of the phosphorus and iron-containing mesoporous zeolite with MFI structure, 32 wt % of pseudo-boehmite, 7 wt % of alumina sol and the balance of kaolin.

The preparation of the hydrotreating catalyst used in the examples is briefly described as follows:

ammonium metatungstate (($NH_4$)$_2W_4O_{13}$·18$H_2O$, chemically pure) and nickel nitrate (Ni($NO_3$)$_2$·18$H_2O$, chemically pure) were weighed and formulated into 200 ml of solution with water. The solution was added to 50 g of alumina carrier, immersed at room temperature for 3 hours, the immersion liquid was treated with ultrasonic waves for 30 minutes during the immersion, cooled, filtered, and dried in a microwave oven for about 15 minutes to obtain a catalyst, designated as Catalyst F. The catalyst has the following composition: 30.0 wt % $WO_3$, 3.1 wt % NiO and a balance of alumina.

The properties of the catalytic conversion catalysts A, B, C, D and the oligomerization catalyst E used in the examples are set forth in Table 2. Catalyst B is a catalytic cracking catalyst available from Qilu Branch of Sinopec Catalyst Co., Ltd. under the trade name MMC-1, Catalyst C is a catalyst with high propylene and gasoline yield available from Qilu Branch of Sinopec Catalyst Co., Ltd. under the trade name RAG-1, Catalyst D is a conventional catalytic cracking catalyst available from Qilu Branch of Sinopec Catalyst Co., Ltd. under the trade name MLC-500, and the oligomerization catalyst E is a zeolite solid acid catalyst available from Qilu Branch of Sinopec Catalyst Co., Ltd. under the trade name RGW-1.

TABLE 2

Properties of the catalysts used in the examples

| Catalyst name | A | B | C | D | E |
|---|---|---|---|---|---|
| Zeolite type | Meso-porous | Meso-porous (main) + macro-porous (minor) | Meso-porous (minor) + macro-porous (main) | Macro-porous | / |
| Aluminum oxide | 50.5 | 51 | 50.2 | 38.4 | 49.8 |
| Sodium oxide | 0.066 | 0.066 | 0.321 | 0.34 | 0.28 |
| Iron oxide | 0.3 | 0.056 | 1.1 | / | / |
| Rare earth | / | / | 2.5 | / | / |
| Apparent density, kg/m$^3$ | 740 | 800 | 700 | 740 | 745 |
| Pore volume, ml/g | 0.33 | 0.22 | 0.40 | 0.28 | 0.67 |
| Specific surface area, m$^2$/g | 251 | 191 | 196 | 234 | 258 |
| Abrasion index, wt %/h | 0.99 | 2.8 | 1.5 | 1.7 | 1.1 |
| Sieving composition, wt % | | | | | |
| 0-40 microns | 18.9 | 27.8 | 20.2 | / | / |
| 40-80 microns | 46.7 | 62 | 50.1 | / | / |
| >80 microns | 34.4 | 10.2 | 29.7 | / | / |

Example 1

This example was conducted in accordance with the process flow shown in FIG. 1, using Feedstock oil A directly as a feedstock for catalytic conversion, on a pilot plant of diameter-transformed riser reactor. Feedstock oil A was fed to the bottom of a first reaction zone I, contacted with Catalyst A at the bottom of the first reaction zone I and subjected to catalytic conversion reaction sequentially in the first reaction zone I and a second reaction zone II. The resulting reaction product and spent catalyst deposited with carbon were separated in a disengager, and the reaction product was split according to distillation range in a product separation unit to obtain dry gas, ethylene, propylene, propane, butane, a fraction comprising $C_4$ olefin, a fraction having a distillation range of <145° C., a fraction having a distillation range of 145-260° C. and a fraction having a distillation range of >260° C.; the fraction having a distillation range of <145° C. was passed to an olefin separation device to further separate BTX, a fraction comprising $C_5$ olefin, a fraction comprising $C_6$ olefin, a fraction comprising $C_7$ olefin, a fraction comprising $C_8$ olefin and n-/iso-paraffins. The content of $C_4$ olefin in the $C_4$ olefin-containing fraction was 90 wt %, the content of $C_5$ olefin in the $C_5$ olefin-containing fraction was 90 wt %, the content of $C_6$ olefin in the $C_6$ olefin-containing fraction was 90 wt %, the content of $C_7$ olefin in the $C_7$ olefin-containing fraction was 90 wt %, and the content of $C_8$ olefin in the $C_8$ olefin-containing fraction was 90 wt %.

The various olefin fractions obtained were fed to different oligomerization reactors, respectively, for oligomerization in accordance with the process flow shown in FIG. 1; in oligomerization reactor 43 and oligomerization reactor 42, the weight ratio of $C_5$ olefin to $C_7$ olefin was 1:0.7, and the weight ratio of $C_4$ olefin to $C_8$ olefin was 1:0.5; a fraction comprising $C_{12}$ olefin was separated using a rectifying column, and recycled to the second reaction zone II of the diameter-transformed riser reactor, and the fraction comprising $C_6$ olefin was directly introduced into the second reaction zone II; the fraction having a distillation range of 145-260° C. was recycled, the fraction having a distillation range >260° C. was hydrogenated under conditions including a hydrogen partial pressure of 18.0 MPa, a reaction temperature of 350° C., a hydrogen-to-oil volume ratio of 1500 and a volume space velocity of 1.5 h$^{-1}$, and the hydrogenation product and the n-/iso-paraffins were recycled to the first reaction zone I at the bottom of the diameter-transformed riser reactor for catalytic conversion reaction. The $C_6$ olefin introduced into the second reaction zone II of the diameter-transformed riser reactor accounted for 10 wt % of the total catalytic conversion feedstock, and the $C_{12}$ olefin introduced into the second reaction zone II of the diameter-transformed riser reactor accounted for 26.9 wt % of the total catalytic conversion feedstock. The operating conditions and product distribution are listed in Table 3.

Comparative Example 1

The operation was substantially the same as in Example 1, except that a conventional catalytic cracking catalyst D was used and the product was split as required in conventional catalytic cracking processes to obtain dry gas, liquefied gas, propylene, gasoline, diesel oil and slurry oil, and no recycle of the catalytic conversion product was performed. The operating conditions and product distribution are listed in Table 3.

TABLE 3

Operating conditions and results of Example 1 and Comparative Example 1

| Item | Example 1 | | Comparative Example 1 |
|---|---|---|---|
| Feedstock oil | Feedstock oil A | Feedstock oil A* | Feedstock oil A |
| Operating conditions (catalytic conversion unit) | | | |
| Reactor | Dual-diameter riser | Dual-diameter riser | Dual-diameter riser |
| Catalyst | A | A | D |
| Riser outlet temperature, °C. | 500 | 500 | 500 |
| Temperature of reaction zone I/II, °C. | 550/500 | 550/500 | 550/500 |
| Reaction time of reaction zone I/II, seconds | 1.0/4.7 | 1.0/4.7 | 1.0/4.7 |
| Catalyst-to-oil weight ratio of reaction zone I/II | 5.0/6.5 | 5.0/6.5 | 5.0/6.5 |
| Steam/feedstock oil weight ratio | 0.10 | 0.10 | 0.10 |
| Operating conditions (oligomerization unit) | | | |
| Catalyst | E | / | / |
| Temperature of $C_4$, $C_8$ olefin oligomerization, °C. | 430 | / | / |
| Pressure of $C_4$, $C_8$ olefin oligomerization, MPa | 2.6 | / | / |
| Weight hourly space velocity of $C_4$, $C_8$ olefin oligomerization, $h^{-1}$ | 2.4 | / | / |
| Temperature of $C_5$, $C_7$ olefin oligomerization, °C. | 400 | / | / |
| Pressure of $C_5$, $C_7$ olefin oligomerization, MPa | 3 | / | / |
| Weight hourly space velocity of $C_5$, $C_7$ olefin oligomerization, $h^{-1}$ | 2.1 | / | / |
| Temperature of $C_4$ olefin oligomerization, °C. | 200 | / | / |
| Pressure of $C_4$ olefin oligomerization, MPa | 2 | / | / |
| Weight hourly space velocity of $C_4$ olefin oligomerization, $h^{-1}$ | 1 | / | / |
| Operating conditions (hydrotreatment unit) | | | |
| Catalyst | F | / | / |
| Temperature, °C. | 350 | / | / |
| Hydrogen partial pressure, MPa | 18.0 | / | / |
| Volume space velocity, $h^{-1}$ | 1.5 | / | / |
| Hydrogen-to-oil volume ratio | 1500 | / | / |
| Product distribution, wt % | | | |
| Dry gas | 3.64 | 3.33 | 3.01 |
| Methane | 0.45 | 0.41 | 0.51 |
| Ethane | 0.36 | 0.32 | 0.38 |
| Liquefied gas | 60.73 | 29.09 | 17.51 |
| Propylene | 47.89 | 12.71 | 5.1 |
| Propylene/propane | / | 4.0 | 3.0 |
| Isobutene/isobutane | / | 2.1 | 0.7 |
| Gasoline | — | 37.39 | 48.81 |
| Diesel oil | — | 17.93 | 18.92 |
| BTX | 26.09 | — | / |
| Slurry oil | — | 3.61 | 3.00 |
| Coke | 9.54 | 8.65 | 8.75 |
| Total | 100.00 | 100.00 | 100.00 |

*Data of Example 1 in column 2 are operating conditions and results for the case where the catalytic conversion reaction was carried out only in the diameter-transformed riser reactor and the resulting catalytic conversion product was not recycled.

Example 2

The test was conducted using Feedstock oil B as the feedstock for catalytic conversion, on a composite reactor as shown in FIG. 2 comprising a riser and a dense phase bed connected in series. The Feedstock oil B was contacted with Catalyst B, and the reaction was carried out in the riser unit of the composite reactor under conditions including a reaction temperature of 650° C., a reaction time of 0.8 seconds, a catalyst-to-oil weight ratio of 20, and a steam-to-oil weight ratio of 0.8; the resulting reaction stream was passed to the dense phase bed unit of the composite reactor for further reaction at a reaction temperature of 580° C., and a weight hourly space velocity of 10 $h^{-1}$ to obtain a spent catalyst and a reaction product. The spent catalyst was regenerated, and the regenerated catalyst was recycled to the riser unit as the catalytic conversion catalyst. The reaction product was split according to distillation range in a product separation unit to obtain dry gas, ethylene, propylene, propane, butane, a fraction comprising $C_4$ olefin, a fraction having a distillation range of <145° C., fraction having a distillation range of 145-260° C. and a fraction having a distillation range of >260° C.; the fraction having a distillation range of <145° C. was passed to an olefin separation device to further separate BTX, a fraction comprising $C_5$ olefin, a fraction comprising $C_6$ olefin, a fraction comprising $C_7$ olefin, a fraction comprising $C_8$ olefin and n-/iso-paraffins. The content of $C_4$ olefin in the $C_4$ olefin-containing fraction was 90 wt %, the content of $C_5$ olefin in the $C_5$ olefin-containing fraction was 90 wt %, the content of $C_6$ olefin in the $C_6$ olefin-containing fraction was 90 wt %, the content of $C_7$ olefin in the $C_7$ olefin-containing fraction was 90 wt %, and the content of $C_8$ olefin in the $C_8$ olefin-containing fraction was 90 wt %.

The various olefin fractions obtained were fed to different oligomerization reactors, respectively, for oligomerization in accordance with the process flow shown in FIG. 1, in oligomerization reactor 43 and oligomerization reactor 42 the weight ratio of $C_5$ olefin to $C_7$ olefin is 1:0.7, and the weight ratio of $C_4$ olefin to $C_8$ olefin is 1:0.5; a fraction comprising $C_{12}$ olefin was separated using a rectifying column, and recycled to the dense phase bed unit, and the fraction comprising $C_6$ olefin was directly introduced into the dense phase bed unit. The $C_6$ olefin introduced into the dense phase bed unit for further cracking accounted for 6.6 wt % of the total catalytic conversion feedstock and the $C_{12}$ olefin accounted for 25.5 wt % of the total catalytic conversion feedstock. The operating conditions and product distribution are listed in Table 4.

Comparative Example 2

The operation was substantially the same as in Example 2, except that the catalytic conversion product was separated and split to obtain dry gas, liquefied gas, propylene, gasoline, diesel oil and slurry oil, and the recycling of the catalytic conversion product was not performed. The operating conditions and product distribution are listed in Table 4.

TABLE 4

Operating conditions and results of Example 2 and Comparative Example 2

| Item | Example 2 | Comparative Example 2 |
|---|---|---|
| Feedstock oil | B | B |
| Operating conditions (catalytic conversion unit) | | |
| Reactor | Riser + dense phase bed | Riser + dense phase bed |
| Riser unit | | |
| Catalyst | B | B |
| Reaction temperature, °C. | 650 | 650 |
| Reaction time, seconds | 0.8 | 0.8 |
| Steam/feedstock oil weight ratio | 0.8 | 0.8 |
| Catalyst/feedstock oil weight ratio | 20.0 | 20.0 |
| Dense phase bed unit | | |
| Reaction temperature, °C. | 580 | 580 |
| Weight hourly space velocity, $h^{-1}$ | 10 | 10 |
| Operating conditions (oligomerization unit) | | |
| Catalyst | E | / |
| Temperature of $C_4$, $C_8$ olefin oligomerization, °C. | 430 | / |
| Pressure of $C_4$, $C_8$ olefin oligomerization, MPa | 2.6 | / |
| Weight hourly space velocity of $C_4$, $C_8$ olefin oligomerization, $h^{-1}$ | 2.4 | / |
| Temperature of $C_5$, $C_7$ olefin oligomerization, °C. | 400 | / |
| Pressure of $C_5$, $C_7$ olefin oligomerization, MPa | 3 | / |
| Weight hourly space velocity of $C_5$, $C_7$ olefin oligomerization, $h^{-1}$ | 2.1 | / |
| Temperature of $C_4$ olefin oligomerization, °C. | 200 | / |
| Pressure of $C_4$ olefin oligomerization, MPa | 2 | / |
| Weight hourly space velocity of $C_4$ olefin oligomerization, $h^{-1}$ | 1 | / |
| Product distribution, wt % | | |
| Dry gas | 13.01 | 11.91 |
| Methane | 3.43 | 3.24 |
| Ethane | 2.45 | 2.33 |
| Liquefied gas | 52.93 | 42.22 |
| Propylene | 35.11 | 19.30 |
| Propylene/propane | / | 6.34 |
| Isobutene/isobutane | / | 2.03 |
| Gasoline | 14.31 | 26.60 |
| BTX | 7.69 | 7.53 |
| Diesel oil | 6.83 | 6.69 |
| Slurry oil | 6.39 | 6.37 |
| Coke | 6.53 | 6.21 |
| Total | 100.00 | 100.00 |

Example 3

The test was conducted using Feedstock oil C as a feedstock for catalytic conversion on a composite reactor as shown in FIG. 2 comprising a riser and a dense phase bed connected in series. The Feedstock oil C was contacted with Catalyst C, and the reaction was carried out in the riser unit of the composite reactor under conditions including a reaction temperature of 530° C., a reaction time of 3.5 seconds, a catalyst-to-oil weight ratio of 8, and a steam-to-oil weight ratio of 0.1; the resulting reaction stream was passed to the dense phase bed unit of the composite reactor for further reaction at a reaction temperature of 500° C., and a weight hourly space velocity of 10 $h^{-1}$ to obtain a spent catalyst and a reaction product. The spent catalyst was regenerated, and the regenerated catalyst was recycled to the riser unit as the catalytic conversion catalyst. The catalytic conversion product was separated to obtain dry gas, ethylene, propylene, propane, butane, a fraction comprising $C_4$ olefin, a fraction comprising $C_5$ olefin, a fraction comprising $C_6$ olefin, a fraction comprising $C_7$ olefin, a fraction comprising $C_8$ olefin and n-/iso-paraffins. The content of $C_4$ olefin in the $C_4$ olefin-containing fraction was 90 wt %, the content of $C_5$ olefin in the $C_5$ olefin-containing fraction was 90 wt %, the content of $C_6$ olefin in the $C_6$ olefin-containing fraction was 90 wt %, the content of $C_7$ olefin in the $C_7$ olefin-containing fraction was 90 wt %, and the content of $C_8$ olefin in the $C_8$ olefin-containing fraction was 90 wt %.

The various olefin fractions obtained were fed to different oligomerization reactors, respectively, for oligomerization in accordance with the process flow shown in FIG. 1, in oligomerization reactor 43 and oligomerization reactor 42, the weight ratio of $C_5$ olefin to $C_7$ olefin is 1:0.7, and the weight ratio of $C_4$ olefin to $C_8$ olefin is 1:0.5; a fraction comprising $C_{12}$ olefin was separated using a rectifying column, and recycled to the dense phase bed unit, and the fraction comprising $C_6$ olefin was directly introduced into the dense phase bed unit. The $C_6$ olefin introduced into the dense phase bed unit for further cracking accounted for 7.8 wt % of the total catalytic conversion feedstock, and the $C_{12}$ olefin accounted for 29.4 wt % of the total catalytic conversion feedstock. The operating conditions and product distribution are listed in Table 5.

Comparative Example 3

The operation was substantially the same as in Example 3, except that the catalytic conversion product was split according to distillation range in the product separation unit to obtain dry gas, liquefied gas, propylene, gasoline, diesel oil and slurry oil, and recycling of the catalytic conversion product was not performed. The operating conditions and product distribution are listed in Table 5.

TABLE 5

Operating conditions and results of Example 3 and Comparative Example 3

| Item | Example 3 | Comparative Example 3 |
|---|---|---|
| Feedstock oil | C | C |
| Operating conditions (catalytic conversion unit) | | |
| Reactor | Riser + dense phase bed | Riser + dense phase bed |
| Riser unit | | |
| Catalyst | C | C |
| Reaction temperature, °C. | 530 | 530 |
| Reaction time, seconds | 3.5 | 3.5 |
| Steam/feedstock oil weight ratio | 0.1 | 0.1 |
| Catalyst/feedstock oil weight ratio | 8 | 8 |
| Dense phase bed unit | | |
| Reaction temperature, °C. | 500 | 500 |
| Weight hourly space velocity, $h^{-1}$ | 10 | 10 |
| Operating conditions (oligomerization unit) | | |
| Catalyst | E | / |
| Temperature of $C_4$, $C_8$ olefin oligomerization, °C. | 430 | / |
| Pressure of $C_4$, $C_8$ olefin oligomerization, MPa | 2.6 | / |
| Weight hourly space velocity of $C_4$, $C_8$ olefin oligomerization, $h^{-1}$ | 2.4 | / |

TABLE 5-continued

Operating conditions and results of Example 3 and Comparative Example 3

| Item | Example 3 | Comparative Example 3 |
|---|---|---|
| Temperature of $C_5$, $C_7$ olefin oligomerization, ° C. | 400 | / |
| Pressure of $C_5$, $C_7$ olefin oligomerization, MPa | 3 | / |
| Weight hourly space velocity of $C_5$, $C_7$ olefin oligomerization, $h^{-1}$ | 2.1 | / |
| Temperature of $C_4$ olefin oligomerization, ° C. | 200 | / |
| Pressure of $C_4$ olefin oligomerization, MPa | 2 | / |
| Weight hourly space velocity of $C_4$ olefin oligomerization, $h^{-1}$ | 1 | / |
| Product distribution, wt % | | |
| Dry gas | 3.80 | 3.72 |
| Methane | 0.90 | 0.87 |
| Ethane | 0.71 | 0.66 |
| Liquefied gas | 41.75 | 23.10 |
| Propylene | 33.85 | 8.56 |
| Propylene/propane | / | 5.3 |
| Isobutene/isobutane | / | 1.0 |
| Gasoline | 24.31 | 43.51 |
| Diesel oil | 19.76 | 19.49 |
| Slurry oil | 3.55 | 3.51 |
| Coke | 6.83 | 6.67 |
| Total | 100.00 | 100.00 |

Example 4

The test was conducted using Feedstock A as a feedstock for catalytic conversion on a pilot plant of the diameter-transformed riser reactor as shown in FIG. 3. Feedstock oil A was fed to the bottom of a first reaction zone I, contacted with Catalyst A at the bottom of the first reaction zone I and subjected to catalytic conversion reaction sequentially in the first reaction zone I and a second reaction zone II. The resulting reaction product and spent catalyst deposited with carbon were separated in a disengager, and the reaction product was split according to distillation range in a product separation unit to obtain dry gas, ethylene, propylene, propane, butane, a fraction comprising $C_4$ olefin, a fraction having a distillation range of <145° C., a fraction having a distillation range of 145-260° C. and a fraction having a distillation range of >260° C.; the fraction having a distillation range of <145° C. was passed to an olefin separation device to further separate BTX, a fraction comprising $C_5$ olefin, a fraction comprising $C_6$ olefin, a fraction comprising $C_7$ olefin, a fraction comprising $C_8$ olefin and n-/iso-paraffins. The content of $C_4$ olefin in the $C_4$ olefin-containing fraction was 90 wt %, the content of $C_5$ olefin in the $C_5$ olefin-containing fraction was 90 wt %, the content of $C_7$ olefin in the $C_7$ olefin-containing fraction was 90 wt %, and the content of $C_8$ olefin in the $C_8$ olefin-containing fraction was 90 wt %.

The various olefin fractions obtained were fed to different oligomerization reactors, respectively, for oligomerization in accordance with the process flow shown in FIG. 1, in oligomerization reactor 43 and oligomerization reactor 42, the weight ratio of $C_5$ olefin to $C_7$ olefin is 1:0.7, and the weight ratio of $C_4$ olefin to $C_8$ olefin is 1:0.5; a fraction comprising $C_{12}$ olefin was separated using a rectifying column, and recycled to the second reaction zone II of the diameter-transformed riser reactor; the fraction having a distillation range of 145-260° C. was recycled, the fraction having a distillation range >260° C. was hydrogenated under conditions including a hydrogen partial pressure of 18.0 MPa, a reaction temperature of 350° C., a hydrogen-to-oil volume ratio of 1500 and a volume space velocity of 1.5 $h^{-1}$, and the hydrogenation product and the n-/iso-paraffins were recycled to the first reaction zone I of the diameter-transformed riser reactor for catalytic conversion reaction. The $C_{12}$ olefin introduced into the second reaction zone II of the diameter-transformed riser reactor accounted for 26.9 wt % of the total catalytic conversion feedstock. The operating conditions and product distribution are listed in Table 6.

Comparative Example 4

The operation was substantially the same as in Example 4, except that the reactor was a composite reactor comprising a riser and a fluidized bed connected in series, the catalyst was catalytic cracking catalyst B, the operation was carried out according to the requirements of catalytic cracking processes, and the product was split according to the requirements of catalytic cracking processes to obtain dry gas, liquefied gas, propylene, gasoline, diesel oil and slurry oil, and the recycling of the catalytic conversion product was not performed. The operating conditions and product distribution are listed in Table 6.

TABLE 6

Operating conditions and results of Example 4 and Comparative Example 4

| Item | Example 4 | | Comparative Example 4 |
|---|---|---|---|
| Feedstock oil | Feedstock oil A | Feedstock oil A* | Feedstock oil A |
| Operating conditions (catalytic conversion unit) | | | |
| Reactor | Dual-diameter riser | Dual-diameter riser | Riser + dense phase bed |
| Catalyst | A | A | B is |
| Riser outlet temperature, ° C. | 500 | 500 | 580 |
| Temperature of reaction zone I/II, ° C. | 550/500 | 550/500 | / |
| Reaction time of reaction zone I/II, seconds | 1.0/4.7 | 1.0/4.7 | / |
| Catalyst-to-oil weight ratio of reaction zone I/II | 5.0/6.5 | 5.0/6.5 | / |
| Catalyst-to-oil ratio of the riser | / | / | 8.0 |
| Steam/feedstock oil weight ratio | 0.10 | 0.10 | 0.20 |
| Bed temperature of the fluidized bed, ° C. | / | / | 580 |
| Weight hourly space velocity of the fluidized bed, $h^{-1}$ | / | / | 10 |
| Operating conditions (oligomerization unit) | | | |
| Catalyst | E | / | / |
| Temperature of $C_4$, $C_8$ olefin oligomerization, ° C. | 430 | / | / |
| Pressure of $C_4$, $C_8$ olefin oligomerization, MPa | 2.6 | / | / |
| Weight hourly space velocity of $C_4$, $C_8$ olefin oligomerization, $h^{-1}$ | 2.4 | / | / |
| Temperature of $C_5$, $C_7$ olefin oligomerization, ° C. | 400 | / | / |
| Pressure of $C_5$, $C_7$ olefin oligomerization, MPa | 3 | / | / |
| Weight hourly space velocity of $C_5$, $C_7$ olefin oligomerization, $h^{-1}$ | 2.1 | / | / |
| Temperature of $C_4$ olefin oligomerization, ° C. | 200 | / | / |

TABLE 6-continued

Operating conditions and results of Example 4 and Comparative Example 4

| Item | Example 4 | | Comparative Example 4 |
|---|---|---|---|
| Pressure of $C_4$ olefin oligomerization, MPa | 2 | / | / |
| Weight hourly space velocity of $C_4$ olefin oligomerization, $h^{-1}$ | 1 | / | / |
| Operating conditions (hydrotreatment unit) | | | |
| Catalyst | F | / | / |
| Temperature, ° C. | 350 | / | / |
| Hydrogen partial pressure, MPa | 18.0 | / | / |
| Volume space velocity, $h^{-1}$ | 1.5 | / | / |
| Hydrogen-to-oil volume ratio | 1500 | / | / |
| Product distribution, wt % | | | |
| Dry gas | 3.64 | 3.33 | 9.01 |
| Methane | 0.45 | 0.41 | 3.51 |
| Ethane | 0.36 | 0.32 | 2.58 |
| Liquefied gas | 60.73 | 29.09 | 37.51 |
| Propylene | 47.89 | 12.71 | 17.1 |
| Propylene/propane | / | 4.0 | 5.5 |
| Isobutene/isobutane | / | 2.1 | 1.4 |
| Gasoline | — | 37.39 | 22.71 |
| Diesel oil | — | 17.93 | 18.92 |
| BTX | 26.09 | — | / |
| Slurry oil | — | 3.61 | 3.30 |
| Coke | 9.54 | 8.65 | 8.55 |
| Total | 100.00 | 100.00 | 100.00 |

*Data of Example 4 in column 2 are operating conditions and results for the case where the catalytic conversion reaction was carried out only in the diameter-transformed riser reactor and the resulting catalytic conversion product was not recycled.

Example 5

Figure 4:
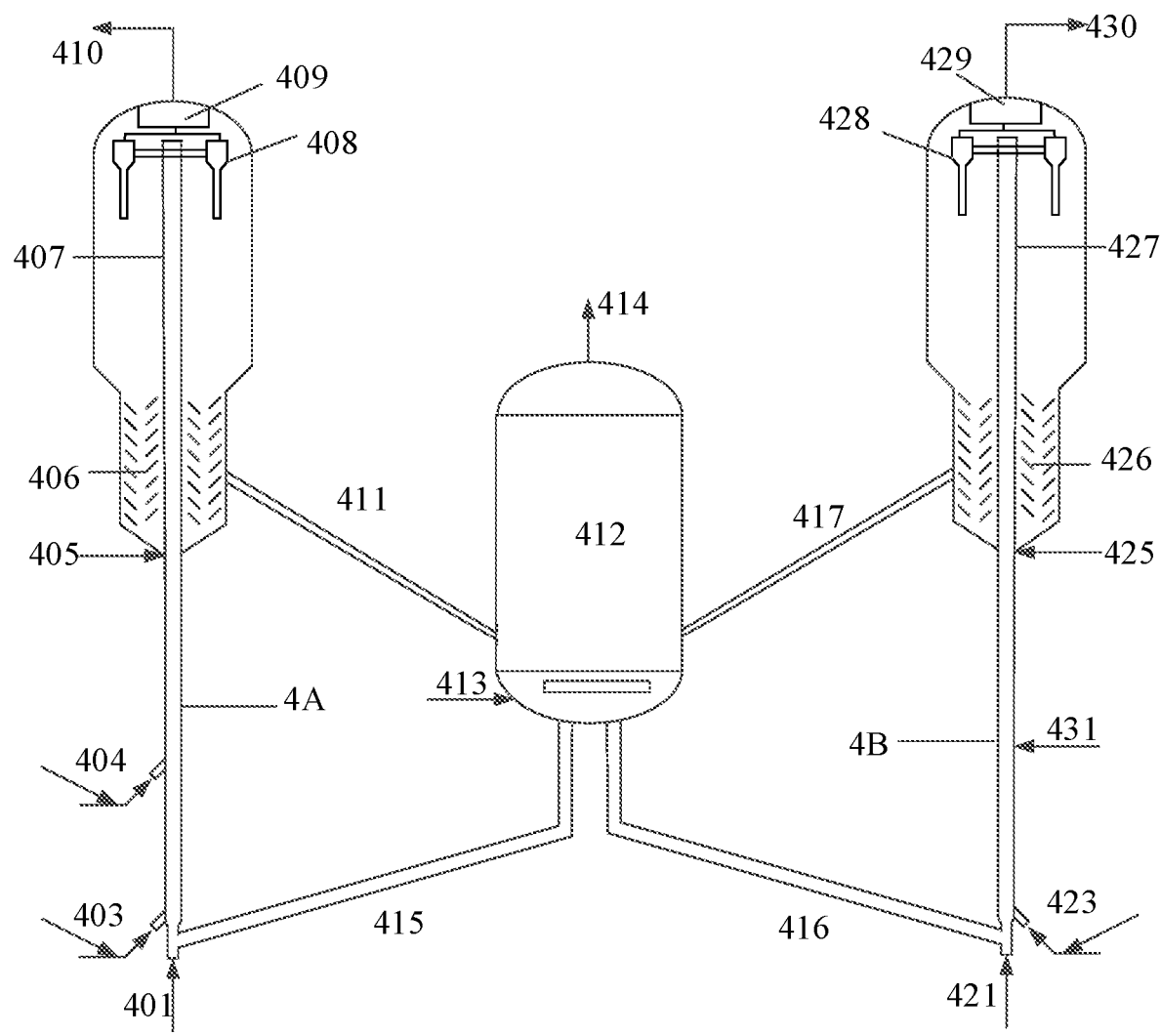
FIG. 4 is a schematic diagram of a fourth embodiment of the process and system of the present application.

The test was conducted using Feedstock oil D as a feedstock for catalytic conversion on a system of double riser reactors as shown in FIG. 4. Feedstock oil D was contacted with Catalyst D, reacted in the first riser reactor under conditions including a reaction temperature at the outlet of the first riser reactor of 530° C., a reaction time of 3.0 seconds, a catalyst-to-oil weight ratio of 6 and a steam-to-oil weight ratio of 0.10 to obtain a spent catalyst and a reaction product. The spent catalyst was regenerated, and the regenerated catalyst was recycled to the first riser reactor as the catalytic conversion catalyst. The reaction product was split in a product separation unit according to distillation range to obtain dry gas, ethylene, propylene, propane, butane, a fraction comprising $C_4$ olefin, a gasoline fraction rich in olefin, diesel oil and slurry oil. The gasoline fraction rich in olefin was fed to the bottom of the second riser reactor, and reacted in the second riser reactor under conditions including a reaction temperature of 530° C., a reaction time of 2.0 seconds, a catalyst-to-oil weight ratio of 6 and a steam-to-oil weight ratio of 0.10.

The fraction comprising $C_4$ olefin was fed to the oligomerization reactor 41 for oligomerization according to the process flow shown in FIG. 1, a fraction comprising $C_{12}$ olefin was separated using a rectifying column, and introduced into the middle part of the second riser reactor for reaction. The operating conditions and the product distribution of the final product obtained by combining the reaction products of the first and second riser reactors are listed in Table 7.

Comparative Example 5

The operation was substantially the same as in Example 5, except that the catalytic conversion product of the first riser reactor was split in the product separation unit according to distillation range to obtain dry gas, liquefied gas, propylene, gasoline, diesel oil and slurry oil, and gasoline accounted for 36.6 wt % of the total catalytic conversion feedstock was recycled to the second riser reactor. The operating conditions and the product distribution of the final product obtained by combining the reaction products of the first and second riser reactors are listed in Table 7.

TABLE 7

Operating conditions and results of Example 5 and Comparative Example 5

| Item | Example 5 | Comparative Example 5 |
|---|---|---|
| Feedstock oil | D | D |
| Reactor | Dual risers connected in parallel | Dual risers connected in parallel |
| Operating conditions (catalytic conversion unit) | | |
| Catalyst | A | A |
| Outlet temperature of the first/second riser, ° C. | 530/530 | 530/530 |
| Reaction time of first/second riser, seconds | 3/2.0 | 3/2.0 |
| Catalyst/feedstock oil weight ratio | 6 | 6 |
| Steam/feedstock oil weight ratio | 0.10 | 0.10 |
| Operating conditions (oligomerization unit) | | |
| Catalyst | E | / |
| Temperature of $C_4$ olefin oligomerization, ° C. | 200 | / |
| Pressure of $C_4$ olefin oligomerization, MPa | 2 | / |
| Weight hourly space velocity of $C_4$ olefin oligomerization, $h^{-1}$ | 1 | / |
| Final product distribution, wt % | | |
| Dry gas | 5.73 | 5.98 |
| Liquefied gas | 32.01 | 31.41 |
| Propylene | 25.31 | 17.06 |
| Gasoline | 23.91 | 24.52 |
| Diesel oil | 24.32 | 24.21 |
| Slurry oil | 5.52 | 5.42 |
| Coke | 8.51 | 8.46 |
| Total | 100.00 | 100.00 |

As can be seen from the results of Tables 3-7, the propylene yield can be increased by 1.5-4 times in the present invention by separating and selectively oligomerizing the $C_4$, $C_5$, $C_7$ and $C_8$ olefins in the catalytic conversion product and recycling the $C_{12}$ olefin produced. In addition, the results of Table 3 also show that, as compared to Comparative Example 1, the catalytic conversion reaction of Example 1 itself can provide a lower alkane yield and a higher propylene yield, while the propylene yield can be further greatly increased by the oligomerization of specific olefins, and the recycle of $C_6$ and $C_{12}$ olefins.

Comparative Example 6

The operation was substantially the same as in Example 1, except that $C_8$ olefin was separated from the catalytic conversion product, and the $C_8$ olefin was recycled to the second reaction zone II of the diameter-transformed riser reactor for further cracking; $C_4$ olefin was fed to an oligomerization reactor for oligomerization, and a fraction comprising $C_8$ olefin was separated using a rectifying column, and recycled to the second reaction zone II; $C_5$ olefin was fed to an oligomerization reactor for oligomerization, and a fraction comprising $C_{10}$ olefin was separated using a rectifying column, and recycled to the second reaction zone II; $C_7$ olefin was fed to an oligomerization reactor for oligomerization, and a fraction comprising $C_{14}$ olefin was separated using a rectifying column, and recycled to the second reaction zone II of the diameter-transformed riser reactor. The operating conditions and product distribution are shown in Table 8.

TABLE 8

Operating conditions and results of Example 1 and Comparative Example 6.

| Item | Example 1 | Comparative Example 6 |
|---|---|---|
| Feedstock oil | Feedstock oil A | Feedstock oil A |
| Operating conditions (catalytic conversion unit) | | |
| Reactor | Dual-diameter riser | Dual-diameter riser |
| Catalyst | A | A |
| Riser outlet temperature, ° C. | 500 | 500 |
| Temperature of reaction zone I/II, ° C. | 550/500 | 550/500 |
| Reaction time of reaction zone I/II, seconds | 1.0/4.7 | 1.0/4.7 |
| Catalyst-to-oil weight ratio of reaction zone I/II | 5.0/6.5 | 5.0/6.5 |
| Steam/feedstock oil weight ratio | 0.10 | 0.10 |
| Operating conditions (oligomerization units)* | | |
| Catalyst | E | E |
| Temperature of $C_5$ olefin oligomerization, ° C. | / | 430 |
| Pressure of $C_5$ olefin oligomerization, MPa | / | 2.6 |
| Weight hourly space velocity of $C_5$ olefin oligomerization, $h^{-1}$ | / | 2.4 |
| Temperature of $C_7$ olefin oligomerization, ° C. | / | 400 |
| Pressure of $C_7$ olefin oligomerization, MPa | / | 3 |
| Weight hourly space velocity of $C_7$ olefin oligomerization, $h^{-1}$ | / | 2.1 |
| Temperature of $C_4$ olefin oligomerization, ° C. | / | 200 |
| Pressure of $C_4$ olefin oligomerization, MPa | / | 2 |
| Weight hourly space velocity of $C_4$ olefin oligomerization, $h^{-1}$ | / | 1 |
| Operating conditions (hydrotreatment unit) | | |
| Catalyst | F | F |
| Temperature, ° C. | 350 | 350 |
| Hydrogen partial pressure, MPa | 18.0 | 18.0 |
| Volume space velocity, $h^{-1}$ | 1.5 | 1.5 |
| Hydrogen-to-oil volume ratio | 1500 | 1500 |
| Product distribution, wt % | | |
| Dry gas | 3.64 | 4.52 |
| Methane | 0.45 | 0.52 |
| Ethane | 0.36 | 0.41 |
| Liquefied gas | 60.73 | 58.56 |
| Propylene | 47.89 | 41.15 |
| Gasoline | — | — |
| Diesel oil | — | — |
| BTX | 26.09 | 26.95 |
| Slurry oil | — | — |
| Coke | 9.54 | 9.97 |
| Total | 100.00 | 100.00 |

*Only the operating conditions of the oligomerization unit of Comparative Example 6 are given in Table 8, and the operating conditions of the oligomerization unit of Example 1 are provided in Table 3.

From the results of Tables 3-8, it can be seen that the recycle of $C_6$, $C_{12}$ olefins in the present invention shows a higher propylene yield than the recycle of $C_8$, $C_{10}$, $C_{14}$ olefins.

The present application is illustrated in detail hereinabove with reference to preferred embodiments, but is not intended to be limited to those embodiments. Various modifications may be made following the inventive concept of the present application, and these modifications shall be within the scope of the present application.

It should be noted that the various technical features described in the above embodiments may be combined in any suitable manner without contradiction, and in order to avoid unnecessary repetition, various possible combinations are not described in the present application, but such combinations shall also be within the scope of the present application.

In addition, the various embodiments of the present application can be arbitrarily combined as long as the combination does not depart from the spirit of the present application, and such combined embodiments should be considered as the disclosure of the present application.

The invention claimed is:

1. A process for producing propylene, comprising the steps of:
    step 1: providing a starting material comprising olefins having 4+ carbon atoms;
    step 2: separating the starting material to obtain a first propylene precursor comprising olefins having $3 \times 2^n$ carbon atoms, wherein n is an integer, a fraction comprising $C_4$ olefin, a fraction comprising $C_5$ olefin, a fraction comprising $C_7$ olefin, and a fraction comprising $C_8$ olefin;
    step 3: subjecting a first portion of the fraction comprising $C_4$ olefin to a first oligomerization to produce a first product, and separating the first product to obtain $C_{12}$ olefin;
    step 4: combining the fraction comprising $C_5$ olefin with the fraction comprising $C_7$ olefin, subjecting the combined fractions to a second oligomerization to produce a second product, and separating the second product to obtain $C_{12}$ olefin;
    step 5: combining a second portion of the fraction comprising $C_4$ olefin with the fraction comprising $C_8$ olefin, subjecting the combined fractions to a third oligomerization to produce a third product, and separating the third product to obtain $C_{12}$ olefin;
    step 6: combining the $C_{12}$ olefin from steps 3, 4, and 5 to produce a second propylene precursor comprising $C_{12}$ olefin; and
    step 7: subjecting the first and second propylene precursor to a catalytic cracking reaction to obtain a reaction product comprising propylene.

2. The process according to claim 1, wherein the oligomerization in each of step 3, step 4, and step 5 is carried out independently in the presence of an oligomerization catalyst and under conditions including:
    a temperature of about 50-550° C., a pressure of about 0.2-8.0 MPa, and a weight hourly space velocity of about 0.1-10 $h^{-1}$, and the oligomerization catalyst being independently selected from the group consisting of phosphoric acid catalysts, acidic resins, silica-alumina solid acid catalysts, zeolite solid acid catalysts, and combinations thereof;
    wherein in step 4, a weight ratio of $C_5$ olefin to $C_7$ olefin in the oligomerization feedstock is about 1:0.7 to about 1:3; and/or wherein in step 5, a weight ratio of $C_4$ olefin to $C_8$ olefin in the oligomerization feedstock is about 1:0.5 to about 1:3.

3. The process according to claim 2, wherein:
the phosphoric acid catalyst is one or more selected from the group consisting of a catalyst formed by loading phosphoric acid on diatomite, a catalyst formed by loading phosphoric acid on activated carbon, a catalyst formed by phosphoric acid-soaked quartz sand, a catalyst formed by loading phosphoric acid on silica gel and a catalyst formed by loading copper pyrophosphate on silica gel;
the silica-alumina solid acid catalyst is a catalyst formed by loading metal ion(s) on alumina and/or an amorphous silica-alumina carrier, wherein the loaded metal ion(s) can be selected from Group VIII metals, Group IVA metals or a combination thereof; and
the zeolite solid acid catalyst comprises about 10-100 wt % of a zeolite and about 0-90 wt % of a matrix, based on the weight of the zeolite solid acid catalyst, wherein the zeolite is one or more selected from the group consisting of one-dimensional zeolites, two-dimensional zeolites, and three-dimensional zeolites.

4. The process according to claim 1, wherein the first propylene precursor has a $C_6$ olefin content of no less than about 40 wt %, based on the weight of the first propylene precursor; and/or
the resulting second propylene precursor has a $C_{12}$ olefin content of no less than about 40 wt %, based on the weight of the second propylene precursor.

5. The process according to claim 1, wherein:
the fraction comprising $C_4$ olefin has a $C_4$ olefin content of about 40-100 wt %, based on the weight of the fraction comprising $C_4$ olefin;
the fraction comprising $C_5$ olefin has a $C_5$ olefin content of about 40-100 wt %, based on the weight of the fraction comprising $C_5$ olefin;
the fraction comprising $C_7$ olefin has a $C_7$ olefin content of about 40-100 wt %, based on the weight of the fraction comprising $C_7$ olefin; and
the fraction comprising $C_8$ olefin has a $C_8$ olefin content of about 40-100 wt %, based on the weight of the fraction comprising $C_8$ olefin.

6. The process according to claim 1, wherein the step 1 further comprises subjecting a hydrocarbon feedstock to a catalytic conversion reaction to obtain a reaction product comprising the starting material,
wherein the hydrocarbon feedstock is selected from petroleum hydrocarbons, other mineral oils, or a combination thereof, wherein the petroleum hydrocarbon is one or more selected from the group consisting of vacuum gas oils, atmospheric gas oils, coker gas oils, deasphalted oils, vacuum residues, atmospheric residues, and heavy aromatic raffinate oils; said other mineral oil is one or more selected from the group consisting of coal liquefaction oil, oil sand oil and shale oil.

7. The process according to claim 6, wherein the catalytic conversion reaction of step 1 and the catalytic cracking reaction of step 7 are carried out in separate reaction units, and the reaction units used in step 1 and step 7 are each independently a fluidized bed reactor; or
the catalytic conversion reaction of step 1 and the catalytic cracking reaction of step 7 are carried out in the same or different parts of a fluidized bed reactor, the fluidized bed reactor is a riser reactor or a composite reactor comprising a riser in combination with a dense phase bed, and wherein the riser reactor is an equal-diameter riser reactor or a diameter-transformed riser reactor.

8. The process according to claim 6, wherein the catalytic conversion reaction of step 1 and the catalytic cracking reaction of step are carried out in the presence of a same catalyst comprising about 1-50 wt % of a zeolite, about 5-99 wt % of an inorganic oxide, and about 0-70 wt % of a clay, based on the weight of the catalyst,
wherein the zeolite is selected from the group consisting of mesoporous zeolites, macroporous zeolites, or a combination thereof, the mesoporous zeolite is selected from the group consisting of ZSM series zeolites, ZRP zeolites or a combination thereof, and the macroporous zeolite is one or more selected from the group consisting of REY zeolites, REHY zeolites, ultrastable Y zeolites and high-silica Y zeolites; or
the catalytic conversion reaction of step 1 and the catalytic cracking reaction of step Z are carried out in the presence of different catalysts, and the catalysts used in step 1 and step each independently comprise about 1-50 wt % of a zeolite, about 5-99 wt % of an inorganic oxide, and about 0-70 wt % of a clay, based on the weight of the catalyst, wherein the zeolite is selected from the group consisting of mesoporous zeolites, macroporous zeolites, or a combination thereof, the mesoporous zeolite is selected from the group consisting of ZSM series zeolites, ZRP zeolites or a combination thereof, and the macroporous zeolite is one or more selected from the group consisting of REY zeolites, REHY zeolites, ultrastable Y zeolites and high-silica Y zeolites.

9. The process according to claim 6, wherein the catalytic conversion reaction of step 1 is carried out in a fluidized bed reactor under reaction conditions including: a reaction temperature of about 420-650° C., a reaction time of about 0.05-20 seconds, a catalyst-to-feedstock weight ratio of about 3:1 to about 15:1, and a steam-to-feedstock weight ratio of about 0.03:1 to about 0.5:1.

10. The process according to claim 9, wherein the catalytic conversion reaction of step 1 is carried out to obtain a gaseous product having
a mass fraction ratio of liquefied gas to dry gas of not less than about 7,
a methane yield of no greater than about 2.0%,
a mass fraction ratio of propylene to propane in the liquefied gas of not less than about 3.5, and/or
a mass fraction ratio of isobutylene to isobutane of not less than about 1.5.

11. The process according to claim 6, wherein the catalytic conversion reaction of step 1 is carried out in a diameter-transformed riser reactor comprising, from bottom to top, a first reaction zone and a second reaction zone having a larger diameter than the first reaction zone,
wherein the reaction conditions in the first reaction zone include: a reaction temperature of about 510-650° C., a reaction time of about 0.05-1.0 second, a catalyst-to-feedstock weight ratio of about 3:1 to about 15:1, and a steam-to-feedstock weight ratio of about 0.03:1 to about 0.3:1; and
the reaction conditions in the second reaction zone include: a reaction temperature of about 420-550° C., and a reaction time of about 1.5-20 seconds.

12. The process according to claim 6, wherein step 2 further comprises:
separating from the catalytic conversion product a fraction having a distillation range <145° C., a fraction having a distillation range of about 145-260° C., a fraction having a distillation range >260° C., optionally a propylene product and the fraction comprising $C_4$ olefin;

separating from the fraction having a distillation range <145° C. the first propylene precursor that comprises $C_6$ olefin, the fraction comprising $C_5$ olefin, the fraction comprising $C_7$ olefin and the fraction comprising $C_8$ olefin;

optionally, separating from the fraction having a distillation range <145° C. n-paraffins and iso-paraffins, and recycling the n-paraffins and iso-paraffins to the catalytic conversion reaction of step 1 or to other reaction device(s);

optionally, recycling the fraction having a distillation range of about 145-260° C. to the catalytic conversion reaction of step 1 or sending it to other reaction device(s); and optionally, subjecting the fraction having a distillation range >260° C. to a hydrotreatment and then recycling it to the catalytic conversion reaction of step 1 or sending it to other reaction device(s), wherein the hydrotreatment is carried out in the presence of a hydrotreating catalyst and under conditions including: a hydrogen partial pressure of about 3.0-20.0 MPa, a reaction temperature of about 300-450° C., a hydrogen-to-oil volume ratio of about 300-2000, and a volume space velocity of about 0.1-3.0 $h^{-1}$;

wherein the hydrotreating catalyst comprises a carrier, a metallic component supported on the carrier, and optionally an additive, wherein the carrier is selected from alumina, amorphous silica-alumina or a combination thereof, the metallic component is selected from Group VIB metal, Group VIII metal or a combination thereof, the additive is one or more selected from the group consisting of fluorine, phosphorus, titanium and platinum, the Group VIB metal is selected from Mo, W or a combination thereof, and the Group VIII metal is selected from Co, Ni or a combination thereof; and wherein the additive is present in an amount of about 0-10 wt %, the Group VIB metal is present in an amount of about 12-39 wt %, and the Group VIII metal is present in an amount of about 1-9 wt %, based on the weight of the hydrotreating catalyst.

* * * * *